(12) United States Patent
Drzewiecki

(10) Patent No.: US 6,272,905 B1
(45) Date of Patent: Aug. 14, 2001

(54) METHOD AND APPARATUS FOR REAL TIME GAS ANALYSIS

(75) Inventor: Tadeusz M. Drzewiecki, Rockville, MD (US)

(73) Assignee: metaSensors, Inc., Rockville, MD (US)

( * ) Notice: Subject to any disclaimer, the term of this patent is extended or adjusted under 35 U.S.C. 154(b) by 0 days.

(21) Appl. No.: 09/468,793

(22) Filed: Dec. 21, 1999

Related U.S. Application Data

(62) Division of application No. 09/104,997, filed on Jun. 26, 1998, now Pat. No. 6,076,392
(60) Provisional application No. 60/055,982, filed on Aug. 18, 1997, and provisional application No. 60/069,422, filed on Dec. 18, 1997.

(51) Int. Cl.$^7$ .......................... G01N 31/00; G01N 27/16; A61B 5/08; G06F 15/42
(52) U.S. Cl. .................. 73/53.01; 73/23.2; 73/30.01; 73/61.44; 73/1 G; 422/83; 422/94
(58) Field of Search .................. 73/53.01, 23.2, 73/23.3, 23.34, 30.01, 31.01, 61.41, 61.44, 1 G; 422/83, 84, 94

(56) References Cited

U.S. PATENT DOCUMENTS

| | | | |
|---|---|---|---|
| 3,698,238 | * 10/1972 | Wall et al. ................. | 73/53 |
| 3,791,200 | 2/1974 | Hayre ..................... | 73/61.1 |

(List continued on next page.)

OTHER PUBLICATIONS

Calkins et al. A Flueric Respiratory and Anesthetic Gas Analyzer; Annals of Biomedical Engineering, vol. 10, pp. 83–96, 1982.

Togawa et al. Biomedical Transducers and Instruments; CRC Press LLC, 1997.

*Primary Examiner*—Hezron Williams
*Assistant Examiner*—David J. Wiggins

(57) ABSTRACT

A method and apparatus for real time gas analysis involving determining individual concentrations of fluid constituents in a mixture of known constituents by measuring properties of the mixture and solving a set of equations, which relate the individual gas concentrations to the measured properties of the mixture, for the unknown individual gas concentrations. The individual concentrations of four gasses in a mixture are determined by: passing the mixture through a flowmeter, a capillary, an orifice, and a sonic oscillator; transducing temperature, pressure and acoustic frequency measurements taken from the sensors; determining the density, viscosity, and the specific heat of the mixture; forming three equations which respectively relate these three properties to individual gas concentrations; and solving the three equations and the constitutive equation which requires that the sum of the concentrations equal unity, for the four unknown individual gas concentrations. A single oscillator can serve as both a sensor (e.g., flowmeter, acoustic velocimeter) and an orifice. The fluidic sensors can be formed as a single chip disposable sensor module. By modifying only the processing software, the same sensors or a subset of the sensors can be used to verify or determine the identity of an unknown gas which is supplied by itself in a pure form or in a mixture of other gasses whose identities are known. By measuring N-1 properties of the gas mixture as a whole, the capabilities of an existing sensor system for measuring M gas concentrations can be extended to measure N additional gas concentrations, provided the identities of the gasses in the mixture are known. Similarly, by modifying only the processing software the same sensor can be used to analyze any sets of gas mixtures.

33 Claims, 19 Drawing Sheets

U.S. PATENT DOCUMENTS

| | | | |
|---|---|---|---|
| 3,927,670 | 12/1975 | Turney et al. | 128/188 |
| 4,150,561 | 4/1979 | Zupanick | 73/23 |
| 4,150,670 | 4/1979 | Jewett et al. | 128/188 |
| 4,196,626 | 4/1980 | Manion et al. | 73/339 A |
| 4,558,220 | 12/1985 | Evans | 250/269 |
| 4,570,675 | 2/1986 | Fenwick et al. | 137/805 |
| 4,634,053 | 1/1987 | Herzfeld et al. | 239/315 |
| 4,665,911 * | 5/1987 | Williams et al. | 128/204.21 |
| 4,670,405 | 6/1987 | Stetter et al. | 436/151 |
| 4,779,451 | 10/1988 | Ezawa et al. | 73/53 |
| 4,847,783 | 7/1989 | Grace et al. | 364/497 |
| 4,907,441 | 3/1990 | Shurmer | 73/23 |
| 5,076,094 | 12/1991 | Frye et al. | 73/19.03 |
| 5,107,920 | 4/1992 | Scotti et al. | 165/109.1 |
| 5,108,466 * | 4/1992 | Klein et al. | 55/20 |
| 5,221,871 | 6/1993 | Fuchs et al. | 310/313 R |
| 5,238,056 | 8/1993 | Scotti et al. | 165/109.1 |
| 5,311,447 * | 5/1994 | Bonne | 364/509 |
| 5,325,704 | 7/1994 | Mariani et al. | 73/24.06 |
| 5,461,562 | 10/1995 | Tabanou et al. | 364/422 |
| 5,465,608 | 11/1995 | Lockshin et al. | 73/24.01 |
| 5,469,369 | 11/1995 | Rose-Pehrsson et al. | 364/497 |
| 5,495,744 | 3/1996 | Ueda | 73/1 G |
| 5,640,995 | 6/1997 | Packard et al. | 137/597 |
| 5,767,387 * | 6/1998 | Wang | 73/23.42 |
| 5,821,405 | 10/1998 | Dickey et al. | 73/53.01 |
| 6,076,392 * | 6/2000 | Drzewiecki | 73/23.2 |

* cited by examiner

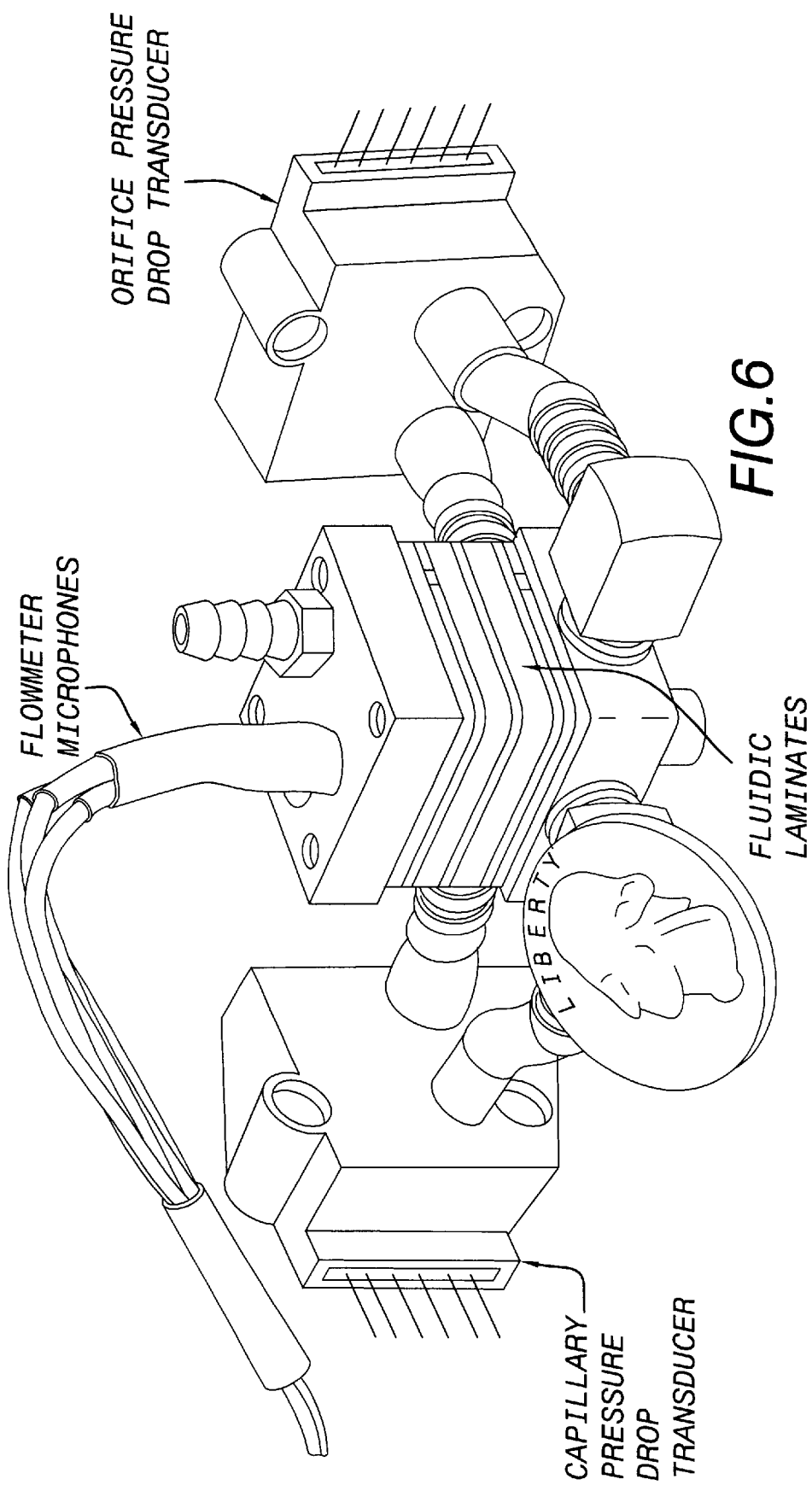

METHOD AND APPARATUS FOR REAL TIME GAS ANALYSIS

CROSS REFERENCE TO RELATED APPLICATIONS

This application is a divisional application of U.S. Patent Application Ser. No.09/104,997, entitled "Method and Apparatus for Real Time Gas Analysis", filed Jun. 26, 1998, now U.S. Pat. No. 6,076,392. The disclosure of the aforementioned patent is incorporated herein by reference in its entity also claims benefit of provisional Ser. Nos. 60/055,982 filed Aug. 18, 1997 and 60/069,422 filed Dec. 18, 1997.

BACKGROUND OF THE INVENTION

1. Field of the Invention

The invention relates to a universal method and apparatus for determining, in real time, the individual concentrations of fluid constituents of any mixture of a predetermined number of fluids using, in the preferred embodiment, fluidic sensors. Further, the invention relates to a method and apparatus for determining or verifying the identity and/or purity of a single gas or an unknown gas in a mixture of gasses.

2. Description of the Prior Art

The determination of the relative concentrations of gasses in a mixture has been the subject of numerous inventions and intensive research over the years. Particularly, when noxious, poisonous or otherwise hazardous gasses are present, knowledge of the amount of such gasses is important to alert personnel in the area of any potential danger. In medical and clinical settings, awareness of the concentrations of respired gasses is important in the determination of patient metabolic conditions, especially the relative and absolute amounts of oxygen and carbon dioxide which provide information on the metabolization of oxygen as well as respiratory functioning. Under operating room conditions, anesthesiologists must be careful in administering anesthesia gasses and do so as a function of metabolic rate, and also must be aware of the absolute amount of anesthetic being provided in order to prevent overdosing or underdosing which would cause a patient to be aware during an operation. Also, when several different potent anesthetics must be administered during a procedure, the net amounts of the anesthetics need to be monitored to prevent overdosing.

Multiple medical gas monitors (MMGMs) continuously sample and measure inspired and exhaled (end-tidal) concentrations of respiratory gasses, including anesthetic gasses during and immediately following administration of anesthesia. These monitors are required since an overdose of anesthetic agent, and/or too little oxygen, can lead to brain damage and death, whereas too little agent results in insufficient anesthesia and subsequent awareness. The current development of these monitoring devices is described in the extensive anesthesia and biomedical engineering literature. Complete and specific information about the principles and applications of these devices is well reviewed in several recent texts (see, e.g., Lake, *Clinical Monitoring*, W B Saunders Co., pp. 479–498 (ch. 8),1990, incorporated herein by reference in its entirety), manufacturer's and trade publications (see, e.g., ECRI, "Multiple Medical Gas Monitors, Respired/Anesthetic", August 1983, incorporated herein by reference in its entirety), and in extensive anesthesia literature describing this equipment and its principles, methods and techniques of operation.

Medical gas monitoring provides the clinician with information about the patients physiologic status, verifies that the appropriate concentrations of delivered gases are administered, and warns of equipment failure or abnormalities in the gas delivery system. These monitors display inspired and exhaled gas concentrations and may sound alarms to alert clinical personnel when the concentration of oxygen ($O_2$), carbon dioxide ($CO_2$), nitrous oxide ($N_2O$), or anesthetic agent falls outside the desired set limits.

Most MMGMs utilize side-stream monitoring wherein gas samples are aspirated from the breathing circuit through long, narrow-diameter tubing lines. A water trap, desiccant and/or filter may be used to remove water vapor and condensation from the sample before the gas sample reaches the analysis chamber. Gas samples are aspirated into the monitor at either an adjustable or a fixed flow rate, typically from 50 to 250 ml/min. Lower rates minimize the amount of gas removed from the breathing circuit and, therefore, from the patient's tidal volume; however, lower sampling flow rates increase the response time and typically reduce the accuracy of conventional measurements. These gas monitors eliminate the exhaust gas through a scavenging system or return certain gas constituents to the patients breathing circuit.

There are several methods and techniques of anesthetic gas monitoring that are currently used. These methods and techniques are briefly reviewed below to distill their intrinsic advantages and disadvantages. A brief comparison is provided that includes both stand-alone and multi-operating room gas monitors that can determine concentrations of anesthetic and respiratory gases in the patient breathing circuit during anesthesia. Much of the research and development of these monitors have followed the long use of similar detector principles from analytical chemistry.

Because of the chemically diverse substances that they measure, MMGMs commonly combine more than one analytical method. Most MMGMs measure concentrations of halogenated anesthetic agents, $CO_2$, and $N_2O$ using nondispersive infrared (IR) absorption technology; however, there are others that use photoacoustic spectroscopy, based on the sound produced when an enclosed gas is exposed to pulsed optical energy. Other MMGMs use a piezoelectric method to measure anesthetic agent concentration. Electrochemical (e.g., galvanic)fuel cells and/or paramagnetic sensors are typically used to measure oxygen concentration, primarily because of their performance characteristics. Some MMGMs also have built-in or modular pulse oximeters to monitor tissue oxygen perfusion, although there is a major problem with the ambiguity between the presence of oxygen and carbon monoxide because hemoglobin bonds with both oxygen and carbon monoxide and conventional single wavelength pulse oximeters cannot distinguish between the two.

Infrared analyzers have been used for many years to identify and assay compounds for research applications. More recently, they have been adapted for respiratory monitoring of $CO_2$, $N_2O$ and halogenated agents. Dual-chamber nondispersive IR spectrometers pass IR energy from an incandescent filament through the sample chamber and an identical geometry but air-filled reference chamber. Each gas absorbs light at several wavelengths, but only a single absorption wavelength is selected for each gas to determine the gas concentration. The light is filtered after it passes through the chambers, and only that wavelength selected for each gas is transmitted to a detector. The light absorption in the analysis chamber is proportional to the partial pressure (e.g., concentration) of the gas. To detect halothane, enflurane, isoflurane, and other related potent anesthetics, most manufacturers use a wavelength range around 3.3 $\mu$m, the peak wavelength at which the hydrogen-carbon bond absorbs light. In one monitor that identifies and quantifies halogenated agents, the analyzer is a single-channel, four-wavelength IR filter photometer. In this monitor, each of four filters (i.e., one for each anesthetic agent and one to provide a baseline for comparison) transmits a specific wavelength of IR energy, and each gas absorbs differently in the selected wavelength bands. In another monitor, the potent anesthetic agent is assayed by determining its absorption at three different wavelengths of light. The (Vickers Medical) Datex Capnomac, a multi-gas anesthetic agent analyzer, is based on the absorption of infrared radiation. This unit accurately analyzes breath-to-breath changes in concentrations of $CO_2$, $NO_2$, and $N_2O$ and anesthetic vapors (See, McPeak et al., "Evaluation of a multigas anaesthetic monitor: the Datex Capnomac", Anaesthesia, Vol. 43, pp.1035–1041, 1988, incorporated herein by reference in its entirety). It is accurate with $CO_2$ for up to 60 breaths/min, and 30 breaths/min for $O_2$, but $N_2O$ and anesthetic vapors show a decrease in accuracy at frequencies higher than 20 breaths/min. The use of narrow wave-band filters to increase specificity for $CO_2$ and $N_2O$ makes the identification of the anesthetic vapors which are measured in the same wave band more difficult. The Inov3100 near-infrared spectroscopy monitor has been offered as a monitor for intracerebral oxygenation during anesthesia and surgery. Studies done on this monitor indicate that it needs a wide optode separation and the measurements are more likely those of the external carotid flow rather than the divided internal carotid circulation (see Harris et al., "Near infrared spectroscopy in adults", Anaesthesia Vol. 48, pp. 694–696, 1993, incorporated herein by reference in its entirety). Almost all non-dispersive infrared (NDIR) devices suffer from cross-sensitivities that may be present, thereby requiring extensive calibration and correction when mixture of gasses flow. The presence of $O_2$, in particular, presents a major problem.

Photoacoustic spectroscopy measures the energy produced when a gas is expanded by absorption of optical radiation; the energy is pulsed by rotating a disk with three concentric slotted sections between the optical source and the measurement chamber. The acoustic pressure fluctuations created occur with a frequency between 20 and 20,000 Hz, producing sound that is detected with a microphone and converted to an electrical signal. Each gas (e.g., anesthetic agent, $CO_2$, $N_2O$) exhibits a pronounced photoacoustic effect at a different wavelength of incident light energy. This method, however, cannot distinguish which halogenated agent is present. A similar microphone can to used to detect the pulsating pressure changes in a paramagnetic oxygen sensor (e.g., magnetoacoustics). The microphone detects the pulsating pressures from all four gases simultaneously and produces a four component signal. A monitor using IR photoacoustic technology has been developed that can quantify all commonly respired/anesthetic gasses except $N_2$ and water vapor (the presence of which adversely affects accuracy). The Bruel & Kjaer Multigas Monitor 1304 uses photoacoustic spectroscopy and also incorporates a pulse oximeter. It has some advantages over the Data Capnomac since it uses the same microphone for detection of all gases, displaying gas concentration with a real-time relationship. There has been found to be a considerable decrease in accuracy when a hybrid sampling tube was used rather than a nafion tube, indicating the need for the additional expense of using a nafion sampling tube to ensure the elimination of water vapor (see McPeak et al., "An Evaluation of the Bruel and Kjaer monitor 1304", Anaesthesia, Vol. 47, pp. 41–47, 1992, incorporated herein by reference in its entirety).

The piezoelectric method is also used to measure the concentration of a selected halogenated agent. The sample is pumped through a chamber containing two crystals: a reference crystal and a second crystal that has been coated with an organophillic compound to adsorb the anesthetic gas. The resulting increase in mass changes the coated crystal's resonant frequency in direct proportion to the concentration of anesthetic gas in the sample, thereby generating a voltage that is displayed as a percentage of vapor. One piezoelectric-based unit has a separate nondispersive IR sensor that differentiates inhalation and exhalation to detect breaths, as well as an integral galvanic fuel cell that measures oxygen concentration before the sampled gas is returned to the breathing circuit. These devices also demonstrate cross-sensitivity to other gasses that may be present.

Mass and Raman spectrometers can measure and identify all respiratory and anesthetic gasses including $N_2$ and in some cases helium. The application of mass spectrometry to the field of monitoring anesthetic gases allows real-time measurement of all inspired and exhaled gasses. Unfortunately, the cost and complexity of this instrumentation has necessitated its being used in a time-sharing fashion among multiple operating rooms. Raman scattering was first heralded as an improvement to mass spectrometry (see Westenskow et al., "Clinical evaluation of a Raman scattering multiple gas analyzer", Anesthesiology, Vol. 70, pp. 350–355, 1989, incorporated herein by reference in its entirety), although there have been some reservations about this technique (see Severinghaus et al, "Multi-operating room monitoring with one mass spectrometer", Acta Anaesthesiol Scan [Suppl] 70:186–187, 1987, incorporated herein by reference in its entirety). The (Ohmeda) Rascal II multigas analyzer, with pulse oximeter, uses a Raman scattering of laser light to identify and quantify $O_2$, $N_2$, $CO_2$, $N_2O$ and anesthetic agents. It is stable and can monitor the gasses including $N_2$ and $CO_2$ accurately for a wide range of concentrations. However, there is a possibility of some destruction of volatile agent during the analysis since the concentration of Halothane does appear to fall when recirculated and there is a gain of the volatile agent of as much as fifteen percent. There is some concern over the reliability of the hardware, software and laser light source (see Lockwood et al., "The Ohmeda Rascall II", Anaesthesia, Vol. 49, pp. 44–53, 1994, incorporated herein by reference in its entirety) which is currently being addressed by others, which necessitates frequent and costly calibration and adjustment.

Other related medical gas monitoring approaches include specific techniques for monitoring oxygen concentration. As described in the above-referenced text by Lake, a commonly used oxygen analyzer detector is based on a polarographic method. In yet another analyzer which uses a galvanic cell, oxygen diffuses through a semipermeable membrane, reaches a reducing electrode, and is carried as a reaction product to another (e.g., reference) electrode, where it frees electrons. The rate at which oxygen diffuses into the cell and generates voltage is directly proportional to the partial pressure of oxygen diffusing through the membrane. Several factors affect the output and lifetime of the cells. During its life, the electrode loses water, some water diffuses out as oxygen which enters the cell while some water is consumed through oxidation, and eventually requires replacement.

Paramagnetic sensors are typically used specifically for measuring oxygen concentration. The design of this sensor is based on oxygen's high degree of sensitivity (e.g., compared to other gasses) to magnetic forces. The sensor includes a symmetrical, two chambered cell with identical chambers for the sample and reference gas (e.g., air). These cells are joined at an interface by a differential pressure transducer or microphone. Sample and reference gases are pumped through these chambers in which a strong magnetic field surrounding the region acts on the oxygen molecules to generate a pressure difference between the two sides of the cell, thereby causing the transducer to produce a voltage proportional to the oxygen concentration. This device, as is the case with most devices, requires frequent calibration, is costly in and of itself, and depends on certain operator skills for proper operation.

Table 1, derived from Eisenkraft et al., "Monitoring Gases in the Anesthesia Delivery System", Anesthesia Equipment: Principles and Applications, Mosby-Year Book, pp.201–220, 1993, incorporated herein by reference in its entirety, provides a summary of methods and techniques to monitor respiratory gasses.

TABLE 1

| METHOD | $O_2$ | $CO_2$ | $N_2O$ | Anes | $N_2$ | He | Ar |
|---|---|---|---|---|---|---|---|
| Mass Spectroscopy | YES | YES | YES | YES | YES | YES | YES |
| Raman Spectroscopy | YES | YES | YES | YES | YES | YES | YES |
| IR - Light Spectroscopy | NO | YES | YES | YES | NO | NO | NO |
| IR - Photo Acoustics | NO | YES | YES | YES | NO | NO | NO |
| Piezoelectric Resonance | NO | NO | NO | YES | NO | NO | NO |
| Polarography | YES | NO | NO | NO | NO | NO | NO |
| Fuel Cell | YES | NO | NO | NO | NO | NO | NO |
| Paramagnetic Analysis | YES | NO | NO | NO | NO | NO | NO |
| Magnetoacoustics | YES | NO | NO | NO | NO | NO | NO |

A review of the background and significance of MMGM would be incomplete without an expression of the impact that patient safety has had on the impetus for recent gains in technology and the need for additional improvements. Clearly, the intrinsic dangers in the conduct of anesthesia have been long understood. However, it has not been until the Department of Anesthesia at the Harvard Teaching Hospital decided to create a set of basic monitoring standards that non-invasive respiratory gas monitoring became widely available and its use common place. The Harvard Medical School Standard for Anesthesia requires:

1) the ability to assure safety and effectiveness of the application of anesthetic agents;
2) simplicity of methods and techniques which translate directly into reliability, low acquisition cost, low cost to service, operate and maintain;
3) appropriate accuracy, precision and stability to monitor relative concentrations of necessary anesthetic gases particularly $CO_2$, $O_2$, and the potent anesthetic gas agents; and
4) appropriate time response and acceptable delays in monitoring changes in relative concentrations of gasses with respect to respiration rates during anesthesia.

Medical malpractice liability insurance companies have lowered their risk liabilities and premiums to anesthesiologists who guarantee to use pulse oximetry and end-tidal $CO_2$ tension monitoring whenever possible (see Swedlow, "Respiratory Gas Monitoring", Monitoring in Anesthesia, pp. 27–50, Boston, Butterworth-Heinemann, 3rd edition, 1993, incorporated herein by reference in its entirety). The argument for providing additional patient safety continues to be a powerful incentive to improve and enhance the methods and techniques to provide increased knowledge of the monitoring of anesthetic gasses.

Safety considerations require that the presence of nitrogen be detected as this provides warning of air embolisms, as well as alerting to possible loss of integrity of the breathing circuit, as air (with $N_2$) is introduced. A major disadvantage of most conventional gas monitors is that they do not measure $N_2$. A major disadvantage of present-day MMGMs which use one or a combination of the above-cited techniques is their high cost. A further disadvantage is that many of these sensors can determine the concentrations of only certain types of gasses or a limited number of gasses.

Fluidic gas concentration sensors offer a low-cost alternative to the devices that use the above techniques. However, known fluidic gas concentration sensors, either oscillators or orifice-capillary pairs, have been capable of detecting concentrations of gasses in a mixture of at most two gasses, and, until only recently, the pressures could not be measured with sufficient accuracy at low cost, to make systems practical.

More particularly, prior fluidic gas concentration sensors, either oscillators (for example, that disclosed in U.S. Pat. No. 3,765,224 to Villarroel et al., the disclosure of which is incorporated herein by reference in its entirety) whose frequency is a function of the speed of sound, and hence, the ratio of specific heats of a gas mixture, or orifice-capillary pairs (for example, that disclosed in U.S. Pat. No. 3,771,348 to Villarroel, the disclosure of which is incorporated herein by reference in its entirety) where the pressure at the junction between the two is a function of density and viscosity of the mixture, were based on measuring the relative concentrations of two gasses in a mixture. Multiple gas analysis may subsequently be accomplished only by physically or chemically separating multiple gas mixtures into multiple two-gas mixtures which may then be separately analyzed. Multiple scrubber approaches, however, cannot be implemented in real time because of the very long delay times associated with passing the gas samples through the volume of a scrubber at the relatively low flow rates associated with the sample streams. Thus, despite the affordability of fluidic sensors, they have not been widely used in MMGMs to measure concentrations of medical gasses during the administration of anesthesia.

Another application for gas analysis in the medical field is the determination or verification of the identity and purity of a gas flowing from a source. Gasses such as oxygen, nitrous oxide, and volatile anesthesia gasses are supplied from sources to patients in operating rooms, intensive care units and hospital rooms. For example, oxygen is often supplied through a wall outlet which is fed from a remotely located oxygen tank. Anesthesia is typically stored in a vaporizer and dispensed by imposing a carrier gas (e.g., $O_2$) through a flow meter which is used to control the amount of anesthesia vapor being supplied. An anesthesia machine may contain several volatile anesthetic agents, each in a separate container with a separate flow meter. While precautions are generally taken to ensure that the correct type of gas is flowing from a source, it is possible for an incorrect gas or a contaminated gas to be supplied. For example, it may be possible for a nitrous oxide tank to be erroneously connected to an oxygen supply line or for one type of anesthesia to be erroneously stored in an anesthesia container labeled as another type of anesthesia. Further, the purity of a gas may be compromised between the source and the point of delivery. For example, an oxygen supply line could be damaged or ruptured, thereby allowing atmospheric gasses to enter the supply line and to be delivered along with a reduced concentration of oxygen.

Use of known gas analyzers to verify the identity and purity of gasses at a source or at a point of delivery would be expensive and impractical in many circumstances. For example, it would be prohibitively expensive to integrate a conventional gas analyzer into every oxygen supply outlet in a hospital. Likewise, it would be expensive to incorporate a conventional gas analyzer into each container of anesthesia gas in a hospital. Further, conventional gas analyzers require periodic calibration which would make such gas analyzers impractical in large numbers. Thus, a low maintenance, lost cost gas analyzer is needed to verify the identity and purity of gasses at a source or point of delivery.

OBJECTS AND SUMMARY OF THE INVENTION

Therefore, in light of the above, and for other reasons that become apparent when the invention is fully described, an object of the present invention is to provide an improved technique for determining the concentrations of fluids, both gaseous and liquid, in mixtures of more than two fluids.

It is another object of the present invention to provide a method and apparatus for augmenting the gas analysis capabilities of conventional gas analyzers using low-cost, reliable fluidic devices, whereby concentrations of a greater number of gasses, including gasses whose concentrations are difficult to determine by conventional means, can be determined.

It is a further object of the present invention to verify the identity and purity of a gas being supplied from a source (either alone or in combination with other gasses) using fluidic devices capable of being integrated with low cost electronic pressure and temperature sensors in order to ensure very low cost and high reliability.

It is yet a further object of the present invention that the fluidic system operate with a minimum of moving mechanical parts requiring no user calibration so that the entire process itself can operate virtually indefinitely.

It is still a further object of the present invention to provide a plurality of utilization modes ranging from permanent installations in operating rooms to portable home-use devices that can be used in residences or temporary situations.

It is another object of the present invention to provide for techniques for providing gas concentration information in a manner conducive to easy readout and compatible with personal computers and other forms of microprocessors.

Another object of the present invention is to provide a disposable fluidic sensor module which can affordably be replaced after each use to simplify sterilization of the gas analyzer.

Yet another object of the present invention is to provide for a universal sensing mechanism which is independent of the gasses being analyzed, use specificity of the analysis being provided only by changes in parameters provided to the analysis software by the user.

Still another object of the present invention is to provide for a means of determining gas concentrations entirely from first physical principles, thereby resulting in a system that never requires calibration or adjustment.

According to the present invention, the individual concentrations of fluid constituents in a mixture of N fluids can be determined in real time by measuring independent properties of the mixture. In particular, N equations, which from first principles, relate the individual fluid concentrations to measured properties of the mixture, are solved for the N unknown individual concentrations of the fluids in the mixture. N-1 properties of the mixture are measured by N-1 sensors, which from cost considerations are preferably fluidic sensors, but may be any other technology devices, and N-1 of the N equations are formed from the determined properties. The Nth equation is the constitutive equation which requires that the sum of the unknown concentrations of the N known constituents be equal to unity.

In an exemplary embodiment, the individual concentrations of three gasses in a mixture of three known gasses are determined by measuring the ambient pressure, temperature and flow rate of the sample flow of the mixture and the subsequent pressure drop of the mixture sample flow across a capillary and across an orifice which may be the supply nozzle of the flowmeter oscillator. The sample flow rate is preferably measured by passing the flow through a fluidic feedback oscillator and measuring the output frequency period which is proportional to transit time. From these measurements, the density and viscosity of the mixture are computed, and the three unknown concentrations of the three known gasses are determined by solving in real time three independent equations (i.e., an equation relating mixture density to the concentrations, an equation relating mixture viscosity to the concentrations, and the constitutive equation). The three-gas analyzer is suitable for monitoring respired, desiccated air (e.g., a three-gas mixture of $O_2$, $CO_2$ and a pseudo-gas composed of $N_2$ with traces of atmospheric inert gasses) and can be used in validation of respiration in critical care medicine, validation of emergency intubation, patient transport (e.g., between care administration areas) and home and out patient respiratory therapy.

By additionally measuring the acoustic velocity in the mixture by using a sonic oscillator, the mixture specific heat may also be calculated. This additional property of the mixture can be related to concentrations of the individual gasses, thereby augmenting the above-described three independent equations with an additional equation. Thus, four independent equations can be solved in real time for unknown concentrations of four gasses in a mixture of four known gasses. In the context of monitoring respired, desiccated anesthesia medical gasses, the four gas analyzer is useful for measuring the concentrations of five gasses. In particular, since the density and viscosity of carbon dioxide and nitrous oxide are virtually indistinguishable, the four independent equations can be solved for the concentrations of $O_2$, $N_2$, a volatile anesthetic and the combined concentration of $N_2O$ and $CO_2$. Since the anesthesia machine removes $CO_2$ from the inspired gasses, the individual concentrations of $N_2O$ and $CO_2$ can be determined by comparing their combined concentration in the exhaled gasses with their combined concentration in the inspired gasses (which is entirely $N_2O$), the difference being the real time concentration of $CO_2$. Thus, the fifth gas is determined from a fifth known condition, that is, that the inspired gas is $CO_2$-free. In the event of loss of the $CO_2$ scrubber (e.g., due to poor maintenance) a breath-to-breath increase will occur; however, having kept track of the minimum value of the combined gas will still provide the value of total $CO_2$ as well as the inspired-to-exhaled ratio.

Preferably, the oscillator flowmeter, sonic oscillator and the capillary are formed as a disposable sensor module comprising a single small, thin, plastic lamination. By attaching (in a separable manner) pressure and temperature sensors at appropriate points, all necessary measurements can be performed. Any one of the oscillator nozzles can serve as the orifice, thereby eliminating the need for a separate orifice. The disposable sensor module is connected via a separable interface to a replaceable transducer module containing the transducers and amplifiers used to measure the characteristics of the mixture, as well as containing the vacuum line for drawing a sample.

Advantageously, low cost, fluidic sensors measure the flow, density, viscosity and speed of sound in gas mixtures. Low-cost micro-electro-mechanical systems (MEMS)-based electronic pressure transducers, low-cost integrated circuit temperature transducers, and ultra-low cost piezoelectric film microphones provide electronic inputs to a microprocessor.

While fluidic measurement of the properties of a gas mixture offers a low-cost alternative to more expensive conventional sensors, the principles of the present invention (i.e., determining individual gas concentrations by solving N equations related to bulk properties of the mixture) can be extended to include any device which measures properties of the mixture as a whole. For example, piezo-electrically-driven surface acoustic wave (SAW) devices have been used to determine density and speed of sound, ultrasonic devices can density, and electrochemical devices can measure viscosity. Depending on their relative cost and accuracy advantages, these devices may be advantageously used in place of fluidic sensors.

In accordance with the present invention, the capabilities of an existing sensor system for measuring M gas concentrations can be extended to measure N additional gas concentrations by measuring N-1 properties of the gas mixture as a whole, regardless of what the gasses are, provided the identities of the gasses in the mixture are known. For example, many existing anesthesia machines capable of measuring five gasses cannot measure the concentrations of nitrogen, carbon monoxide and helium. By augmenting such a five-gas monitor with the fluidic sensors of the present invention, concentrations of these additional gasses can be measured with little additional expense.

The introduction of a new anesthetic agent to the market normally requires the development of a new sensor or at least the identification of a new absorption wavelength with attendant costly changes in hardware. With the universal sensor of the present invention, only the new agent's physical properties need to be programmed into the software, thereby requiring no hardware changes.

Formation and solution of the N equations for the individual concentrations of N gasses typically require that the identity of the N gasses be known, together with their inherent individual properties of the gasses, such as density, viscosity, and specific heat. However, while determining individual concentrations of gasses, the sensor system of the present invention can also determine or verify the identity of an unknown gas in a pure form or in a mixture of other, known gasses.

In accordance with one embodiment, the fluidic sensors of the present invention can be used to determine or verify the identity of a gas flowing from a source. Specifically, the identity of a single, unknown gas can be determined by fluidically measuring properties of the gas, such as density and viscosity, and comparing the measured values to known properties of a gas (e.g., in a look-up table). The identity of the unknown gas can be verified or determined by matching the measured values to those of a known gas.

In accordance with another embodiment of the present invention, the same fluidic measurement device can be used to determine the identity of one unknown gas in a mixture of N gasses of unknown concentrations, where the identities of the other N-1 gasses in the mixture are known. According to one approach for identifying the unknown gas, N properties of the gas mixture are measured; N-1 of the properties are used to generate N-1 equations which, together with the constitutive equation, are solved for N concentrations, where the properties of the unknown constituent are assumed to be those of a particular gas; the computed N concentrations and the measured value of the Nth property of the mixture are used to calculate the Nth property of the unknown gas which is then compared to the known Nth property of the gas assumed to be the unknown gas (for purposes of calculating the concentrations); and different gasses are tried (i.e., assumed to be the unknown gas) in this process until the comparison yields a match or all potential gasses have been tried without a successful match. This approach provides an absolute identification of the unknown gas, since a match cannot occur with an incorrect gas.

According to another approach, where there is a sufficient concentration of the unknown gas, only N-1 (rather than N) properties of the gas mixture are measured and used to generate N-1 equations which, together with the constitutive equation, are solved for N concentrations, where the properties of the unknown constituent are assumed to be those of a particular gas. If the unknown gas was assumed to be a gas other than the correct gas, the solution to the equations will yield concentrations that are not within predetermined expected ranges for at least one of the gasses; conversely, if the unknown gas was assumed to be the correct gas, the solution to the equations will yield values of individual concentrations that are within expected ranges (i.e., a match). Different gasses are tried (assumed to be the unknown gas) in this process until a match is found or all potential gasses have been tried. This approach provides a probable identification of the unknown with a very low probability of error and, relative to the previously-described approach, requires one less property of the mixture to be determined (or can identify an unknown gas in a mixture having one additional gas).

All of the above gas analyses can be performed with the same sensors; only the processing software varies with the different applications. The mixture properties are preferably calculated from measurements made with fluidic sensors that output pressure, acoustic frequency, and temperature, which can be transduced electronically with very small, rugged, durable, low cost transducers. Further, no user calibration of the sensors is required, thereby further reducing the manufacturing and operational costs.

The above and still further objects, features and advantages of the present invention will become apparent upon consideration of the following definitions, descriptions and descriptive figures of specific embodiments thereof wherein like reference numerals in the various figures are utilized to designate like components. While these descriptions go into specific details of the invention, it should be understood that variations may and do exist and would be apparent to those skilled in the art based on the descriptions herein.

BRIEF DESCRIPTION OF THE DRAWINGS

FIG. 6 is a perspective view of a three-gas analyzer constructed with fluidic integrated circuit laminations and external, separable, pressure transducers in accordance with the present invention.

DESCRIPTION OF THE PREFERRED EMBODIMENTS

The following detailed explanations of FIGS. 1–13 and of the preferred embodiments reveal the method and apparatus of the present invention. Although the following description is primarily concerned with medical gas analyzers, the present invention is not limited to the preferred embodiment but is applicable to other gas analysis applications, including, but not limited to, industrial production of gasses, atmospheric analysis, pollution tracking and other applications for the detection and analysis of chemical and biological agents. In addition, the present invention is not limited to a specific number of gasses that are in a mixture or for that matter only fluidic sensors, but rather, since properties of gasses can be measured using a variety of low cost electronic and hybrid electro-fluidic devices, the present invention may extend to low cost scientific gas analysis of large numbers of gasses. Furthermore, the present invention is not limited to the analysis of only gasses, because it should be recognized that substantially the same methods and apparatus may be applied to the analysis of mixtures of liquid fluids as well, as long as sufficient differences in mixture properties occur due to the changes of concentrations of the constituents of the fluids.

In accordance with the present invention, individual concentrations of fluid constituents of a mixture of N known fluids are determined by measuring characteristics of the mixture flowing through a number of sensing devices, determining N-1 properties of the mixture from the measured characteristics, establishing N-1 equations relating the individual concentrations of the fluid constituents to the N-1 properties of the mixture, and solving the N-1 equations and a constitutive equation in real time for the individual concentrations of the fluid constituents.

More particularly, individual concentrations of constituent gasses in a mixture of three known gasses can be determined by fluidically measuring any two independent properties of the mixture. For example, by determining the density and viscosity of the mixture (or viscosity and specific heat, or density and specific heat), the three unknown concentrations of the three known gasses in the three-gas mixture can be determined by solving three independent equations which express relationships of the unknown concentrations to the properties of the mixture.

Figure 1:
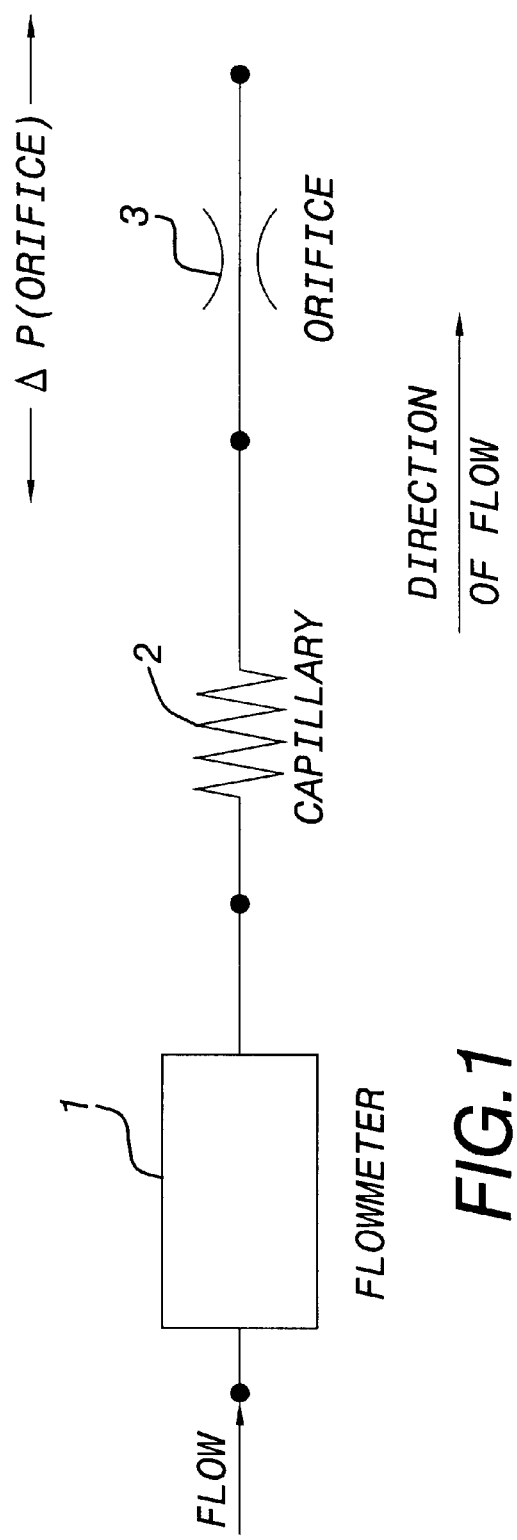
FIG. 1 is a schematic representation of an analog circuit of a flowmeter, capillary and orifice arranged in series.

FIG. 1 is a schematic representation of a gas concentration sensor comprising a property-independent flowmeter 1, a capillary 2 and an orifice 3, which can be used to determine individual concentrations of constituent gasses in a mixture of three known gasses. The viscosity ($\mu$) and density ($\rho$) of the mixture can be determined by measuring: the ambient pressure ($P_{atm}$); the frequency ($f_Q$) of a fluidic flowmeter oscillator when flowmeter 1 is a fluidic feedback oscillator flowmeter; the pressure drop ($\Delta P_C$) across capillary 2; and the pressure drop ($\Delta P_O$) across orifice 3 in accordance with the following equations:

$$\Delta P_c = k_1 \mu Q + k_2 \rho Q^2 \qquad (1)$$

where:

$$k_1 = 12 L_c \left( b_c/h_c + h_c/b_c + \frac{1}{2} \right) \Big/ ([b_c h_c])^2;$$

$$k_2 = 1/[2(h_c b_c)^2];$$

$$\Delta P_o = k_3 \mu Q + k_4 \rho Q^2; \qquad (2)$$

where:

$$k_3 = 12 L_o \left( b_o/h_o + h_o/b_o + \frac{1}{2} \right) \Big/ ([b_o h_o])^2;$$

$$k_4 = 1/[2(h_o b_o)^2]; \quad \text{and}$$

$$Q = k_Q \Big/ \left[ 1/f_Q - k_a \rho^{\frac{1}{2}} \right] \qquad (3)$$

where:

$$k_Q = 32 b_a^2 h_a;$$

$$k_a = 2 L_a \Big/ (P_{atm} \gamma)^{\frac{1}{2}}$$

where $b_c$, $h_c$, and $L_c$ are respectively the width, height and length of capillary 2 with rectangular cross-section, $b_0$, $h_O$, and $L_0$ are respectively the width, height and length of orifice 3 with rectangular cross-section, Q is the volumetric flow rate through the flowmeter 1, $b_a$, $h_a$, and $L_a$ are respectively the width, height and acoustic path length through an oscillator flowmeter 1, and y is the mixture ratio of specific heats which is assumed to be constant. This is valid because the acoustic correction ($k_a \rho^{1/2}$) is very small, and the variation of the correction is also small, resulting in a virtually indiscernible error. In the three-gas analyzer embodiment, the ratio of specific heats is not determined from measurements and must be estimated. For example, for respired gasses (not containing anesthesia), the ratio of specific heat can be estimated to be $\approx 1.4$.

Pressure may be measured by any number of state-of-the-art electronic pressure transducers, but in order to keep the cost low, a low-cost, integrated circuit (IC) semi-conductor strain gage pressure transducer (MEMS-based) can be used (which have only recently become available, i.e., in the last two years), provided the transducer has sufficient dynamic range, that is, that the minimum resolvable pressure should be approximately 1/10,000th to 1/40,000th of the maximum measurable pressure. This pressure measurement is, of course, performed independent of the properties of the gas.

Equations 1–3 contain three unknowns (flow rate Q, viscosity $\mu$, and density $\rho$); thus, these three equations can be solved for the unknowns, and the viscosity $\mu$ and density $\rho$ of the mixture can be determined therefrom. It should be understood that equations 1–3 describe the inherent relationships between the characteristics of the mixture in flow devices of a particular geometry (i.e., the frequency in an oscillator and the pressure drops in a capillary and in an orifice) and the physical properties of the mixture (i.e., density, viscosity and flow rate). It will be understood that these equations vary with different sensor geometries (e.g., non-rectangular cross-sections). Further, higher order terms can be included for greater precision. Conversely, the equations can be simplified to include only first order terms at the potential expense of some precision. See for example, equations (1) and (2) in the aforementioned provisional patent applications Ser. Nos. 60/055,982 and 60/069,422 which do not include higher order terms. In these simplified equations, the pressure drop across the orifice is assumed to be proportional to the density and to the square of the flow rate (and independent of viscosity), and the pressure drop across the capillary is assumed to be proportional to the viscosity and to the flow rate (and independent of density), where the flow rate is assumed to be proportional to the oscillator frequency (and totally independent of gas properties, including density and specific heat). Thus, while the density and viscosity (and flow rate) are determined from the oscillator frequency and the orifice and capillary pressure drops based on inherent relationships, it will be understood that the present invention is not limited to any particular set of equations for determining the density and viscosity or any other properties of the mixture.

Figure 2B:
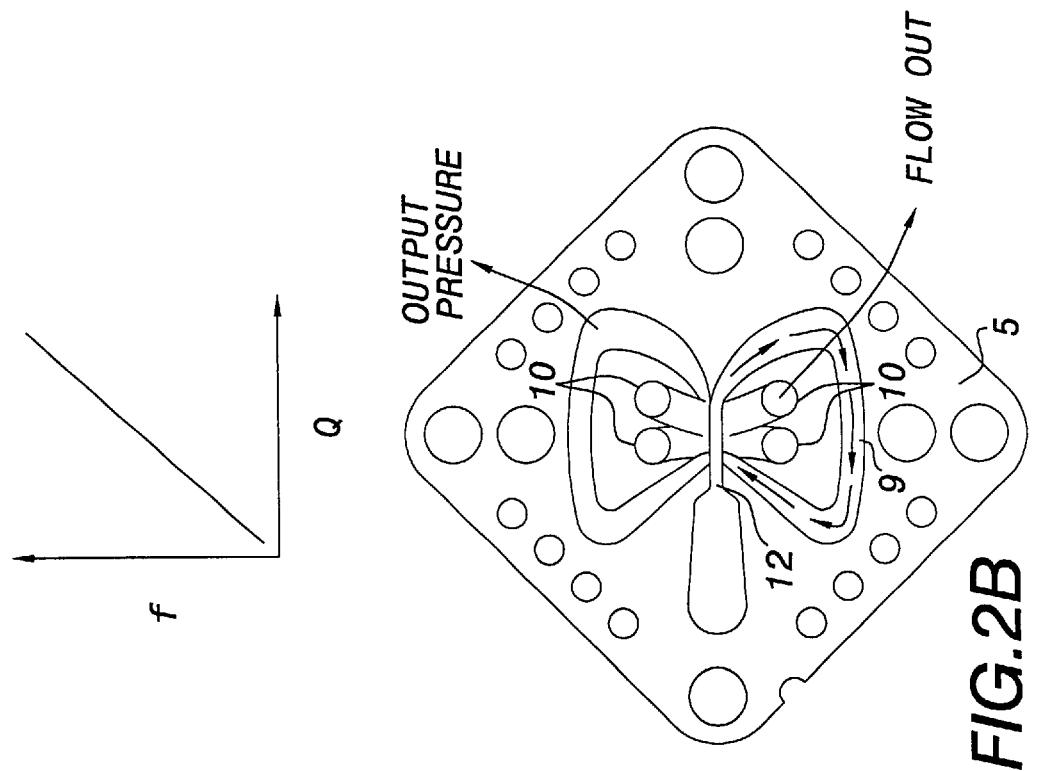
FIG. 2b schematically depicts the second half of a cycle of the operation of a conventional fluidic oscillator flowmeter.
Figure 2A:
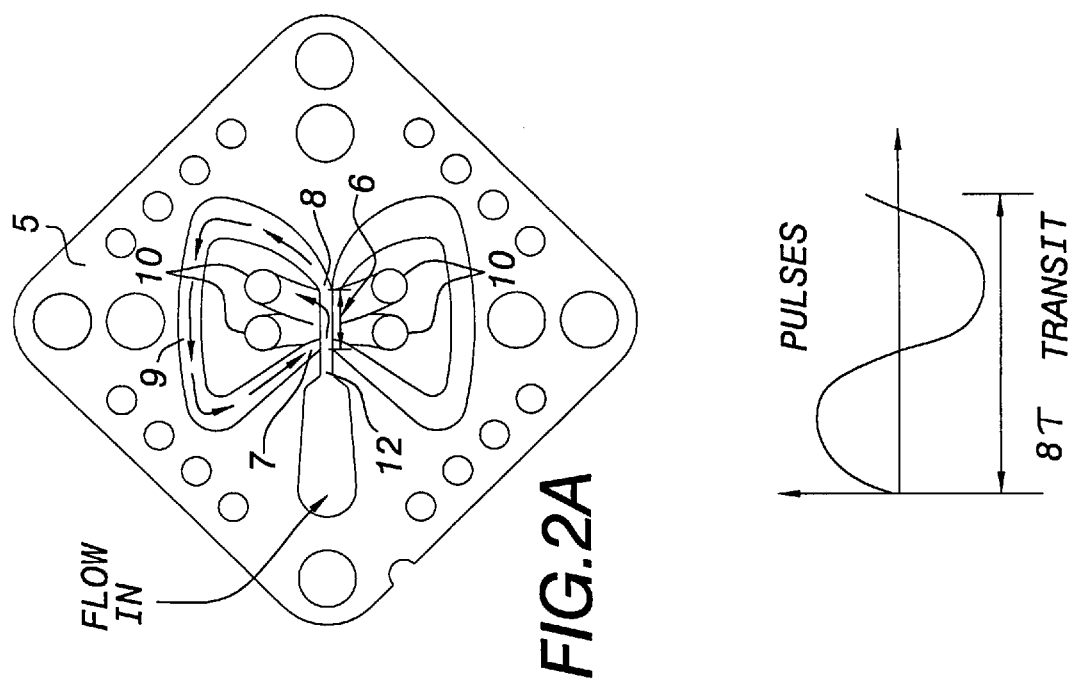
FIG. 2a schematically depicts half of a cycle of the operation of a conventional fluidic oscillator flowmeter.
Figure 3:
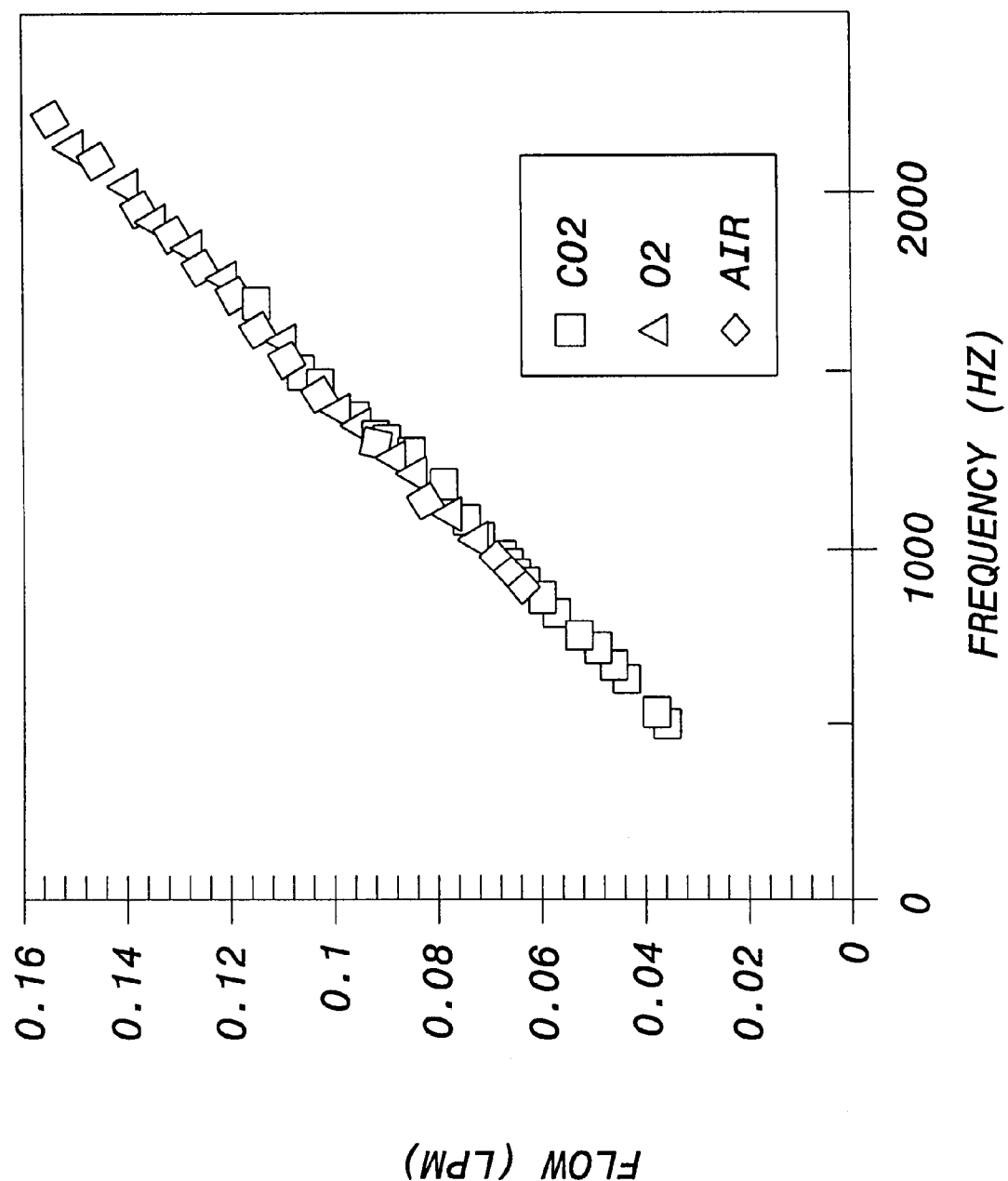
FIG. 3 presents data in graphical form showing the linear dependence of oscillator frequency on through flow in one flowmeter that is used in the present invention, illustrating that the linear flow-frequency characteristic of the flowmeter is independent of which gas is flowing.

FIGS. 2a and 2b illustrate the operation of a fluidic amplifier feedback oscillator flowmeter which can be used as flowmeter 1 in the system of the present invention. Referring to FIG. 2a, the mixture flow passes into the amplifier 5 through a supply nozzle 12, and the jet oscillates by using negative feedback. Fluid flow transit time measurement using a fluidic amplifier feedback oscillator flowmeter 5 has been the subject of numerous previous inventions (e.g., U.S. Pat. No. 3,640,133 to Adams, the disclosure of which is incorporated herein by reference in its entirety) where the period of oscillation is proportional mainly to the transit time of the gas across the transit distance 6 of the fluidic amplifier 5. In general, the period is made up of two parts; the transit time of the fluid flow from the inputs 7 to the outputs 8 (transit distance 6) and the feedback time of the acoustic signal through the outputs back to the inputs through the feedback line 9. Vents 10 collect the fluid flow and pass the fluid to an exhaust port or, in the present implementation, connect to the downstream orifice and capillary. By making the fluid transit time long compared with the acoustic feedback (i.e., by making the acoustic feedback path 9 short and the flow velocity low), the frequency is essentially inversely proportional to only transit time and thus directly proportional to the velocity or flow rate. Since fluid transit time does not depend at all on any gas properties, frequency is therefore largely independent of density and viscosity and is essentially dependent only on flow which is the product of the nozzle area times the transit distance divided by the transit time which in the period of the oscillation frequency. FIG. 2b shows the second half of the oscillation cycle. FIG. 3 shows the calibration for one such oscillator with feedback around a 2.1:1 aspect ratio, ten mil nozzle width, standard Government C/2-format51021 fluidic amplifier. The calibration is the same regardless of the gas (e.g. air, oxygen or carbon dioxide). In fact, it is the same if the fluid is water. The frequency is completely linear up to flow rates of as much as 100 mL/minute for all gasses.

Note that, strictly speaking, even under the foregoing conditions, the oscillator frequency depends at least to some degree on the density and the ratio of specific heats of the sample gas (due to the acoustic feedback time component), as seen from equation (3). Thus, where the ratio of specific heats can be accurately estimated, it is desirable to use equation (3) to determine the flow rate. However, where the ratio of specific heats is not measured and is difficult to estimate (e.g., where anesthetic gas is present), the assumption that flow rate is proportional to the oscillator frequency and independent of gas properties still may provide acceptable results albeit with some small loss of accuracy.

The equations from which the constitute gas volume concentrations are determined are formulated as described in the following paragraphs.

The density of a mixture of gasses, $\rho_{mix}$, is equal to the sum of the products of the concentrations, $C_i$, and the specific densities, $\rho_i$, as determined by applying the law of conservation of matter:

$$\rho_{mix} = \Sigma \rho_i C_i \tag{4}$$

The viscosity of a gas mixture is related to the concentrations of the individual gas components, as determined from the principles of the kinetic theory of gasses, and as shown by the relationship between mixture viscosity and individual concentrations (see Golubev, "Viscosities of Gasses and Mixtures", NTIS Doc. TT70-50022, 1970, incorporated herein by reference in its entirety), which relationship is given by:

$$\mu_{mix} = \Sigma [C_i \mu_i / [C_i + \Sigma C_j \phi_{ij}]] i=1, \ldots, k; j \neq i \tag{5}$$

where $\phi_{ij} = [1+(\mu_i/\mu_j)^{1/2}(M_j/M_i)^{1/4}]^2 / 2.828[1+M_i/M_j]^{1/2}$,
k is the number of constituents, and $M_i$ is the known molecular weight of the ith component of the mixture.

If only three-gas mixtures are of interest, the third equation relating the constituent concentrations is the constitutive equation, which states that the sum of the volume concentrations of all of the gasses must equal unity, $$\Sigma C_i = 1 \tag{6}$$

The resulting system of three algebraic equations can be uniquely solved, in real-time, for the individual concentrations, $C_i$. A microprocessor, or other computational mechanism (e.g., a personal computer, etc.) can be readily programmed to solve this set of equations.

Figure 4:
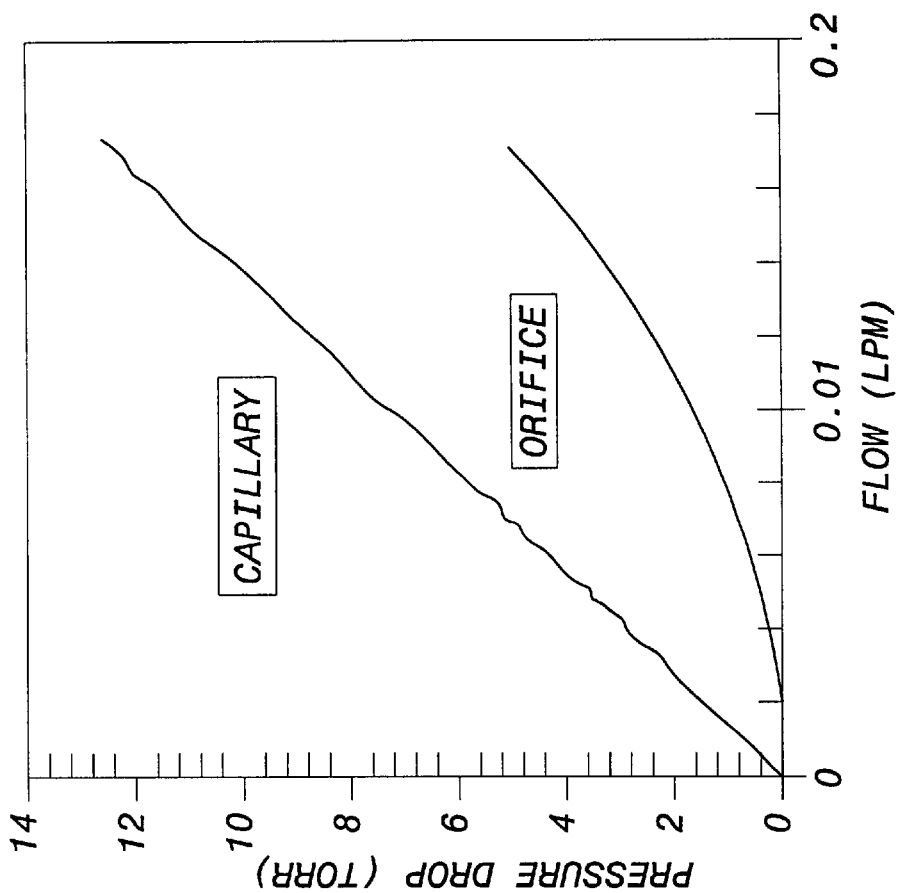
FIG. 4 graphically shows the relationships between the pressure drop and flow for a capillary resistor and orifice used in one embodiment of a three-gas analyzer.

The characteristics of the sensing capillary and orifice are typically shown in FIG. 4, and are chosen in such a manner to minimize the amount of flow that needs to be sampled under operating room conditions (i.e., 50–60 ml/min, or less than half that sampled by conventional IR devices).

Equations (1)–(6) may be programmed on a microprocessor or computer, and voltage data from pressure transducers for, $\Delta P_o$ and $\Delta P_c$, and the output of a frequency-to-voltage (F/V) converter (e.g., Burr-Brown monolithic frequency-to-voltage IC chip), which gives a voltage proportional to flowmeter frequency, $f_{flowmeter}$, may be acquired using appropriate analog-to-digital converters. In addition, since the values of the density and viscosity of the known constituents depend on absolute pressure and temperature (e.g., $\rho_i$ and $\mu_i$ in equations 4 and 5), these two parameters must also be measured, giving rise to two additional voltages that must be provided to the microprocessor. The resultant concentrations may be plotted in real time on a computer CRT or LCD screen in multiple colors in separate traces, or in any other convenient manner.

Figure 5A:
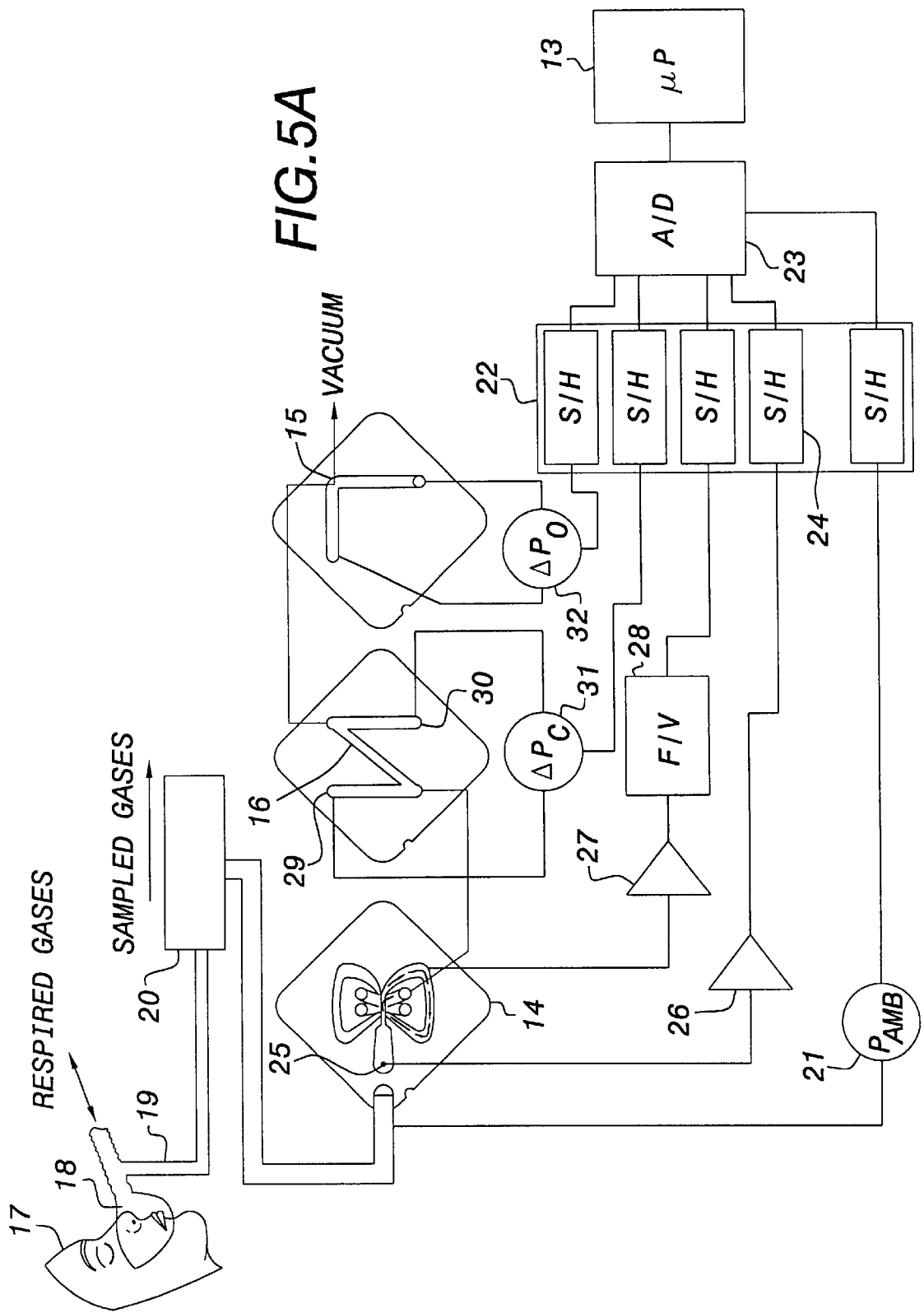
FIG. 5a is a schematic representation of a three-gas analyzer in accordance with the present invention.

An example of a gas analysis system including a flowmeter-capillary-orifice structure capable of three-gas analysis in a monitor for determining concentrations of constituents within respired gasses is illustrated in FIG. 5a. The monitor essentially includes a microprocessor board 13 (e.g., stand alone or within a computer) and a multi-use fluidic gas sensor having a fluidic circuit with an oscillator flowmeter 14 in series with an orifice 15 and a capillary 16. A patient 17 inspires and exhales into a face mask 18, and a side stream sampling port 19 samples the gas near the face mask 18. Sample gas passes through a desiccant 20 which removes any water vapor (which comprises of a fourth gas) that might affect readings. Prior to entering the oscillator flowmeter 14, the ambient absolute pressure of the sample is measured by a pressure sensor 21 and directed to microprocessor 13 via a multiplexer 22 and an analog-to-digital (A/D) converter 23. Multiplexer 22 includes sample and hold registers 24 corresponding to each signal sent to microprocessor 13 from the sensors.

Temperature sensor 25 outputs a voltage proportional to the ambient gas temperature, wherein the output is amplified by electronic amplifier 26 and directed to microprocessor 13 via multiplex 22 and A/D converter 23. The densities and viscosities of the individual gasses are precisely known functions of temperature and pressure; thus, the measured absolute pressure and temperature are utilized to determine the densities and viscosities of the constituent gasses which are needed to determine the gas concentrations (e.g., see equations (4) and (5)).

The sample flow rate is then measured in the oscillator flowmeter 14. A pair of low-cost electret microphones (not shown) or ultra-low cost piezo-electric film microphones pick up two 180° out-of-phase oscillating pressure signals in each feedback leg and are electrically differenced (in order to cancel out ambient noise which is in phase on both microphones) and amplified by an electronic amplifier 27. This amplified periodic signal may be fed into a frequency-to-voltage (F/V) converter 28, and a voltage proportional to the flow rate is applied to the microprocessor 13 via multiplexer 22 and A/D converter 23. Alternatively, a high speed frequency counter may read the frequency directly in the microprocessor.

The flow exits the flowmeter 14 and enters into a capillary resistor 16. The pressures at the ports 29 and 30 at either end of the capillary are fed into a differential pressure transducer 31, such as a low-cost micro-electro-mechanical systems (MEMS)-based electronic pressure transducer(e.g., Data Instruments SURSENSE transducer), and the output voltage is transmitted to the microprocessor 13 via multiplexer 22 and A/D converter 23. The flow then continues through orifice 15 and the pressure at the ports, representing the upstream and downstream pressures across the orifice 15, is measured by yet another differential pressure transducer 32. The voltage from transducer 32 is transmitted to microprocessor 13 via multiplexer 22 and A/D converter 23. In the embodiment shown in FIG. 5a, a vacuum source downstream of orifice 15 provides the negative pressure to sample breath through the sensors. Alternatively, the flow may be driven through the circuit by the patient's breath pressure provided sufficient pressure can be guaranteed (this is not always possible with respiratorily compromised patients or those who are not breathing spontaneously).

Microprocessor 13 can drive a display (not shown), such as a CRT which continuously may display the concentrations of any or all of the three gasses as well as providing any desired numeric outputs, such as respiration rate, numeric values of concentrations, as well as any limits. Optionally, the display may be a liquid crystal display (LCD), wherein the device is a compact battery-operated device with a detachable disposable sensor, wherein the sensors are small enough to be located right on a patient mask or tube. This permits the device to check exhaled oxygen and carbon dioxide at any desired location. Use of electronics with memory provides for recall of previous data for comparison. Also, the microprocessor may be programmed to provide visual and aural alarms in the event of particular occurrences such as overdosing, poor metabolization of oxygen, low or high respiration rates and any other functions as may be desired.

The system produces a real time output of individual concentrations of constituent gasses with no artifacts. The response time of less than 100 ms is fast enough and the side stream sample size is small enough for accurate monitoring of neonates and children.

The embodiment of FIG. 5a may be utilized in various locations, such as the home within a home therapy device, or ambulances and other locations experiencing field trauma within an emergency medicine device for validating ventilation and checking for proper intubation of a patient. In this case, the three respired gasses are oxygen, carbon dioxide, and a known, fixed mixture of nitrogen, argon and other trace gasses. This nitrogen mixture gas remains constant in its constituent concentrations, none being metabolized. The three-gas monitor may be used with ventilator-dependent patients, patients with respiratory insufficiencies or patients having or suspected of having a compromised respiratory system wherein the monitor may be used in various locations, such as ambulances, hospitals and/or sub-acute care facilities, and during patient transport between these facilities.

Figure 5B:
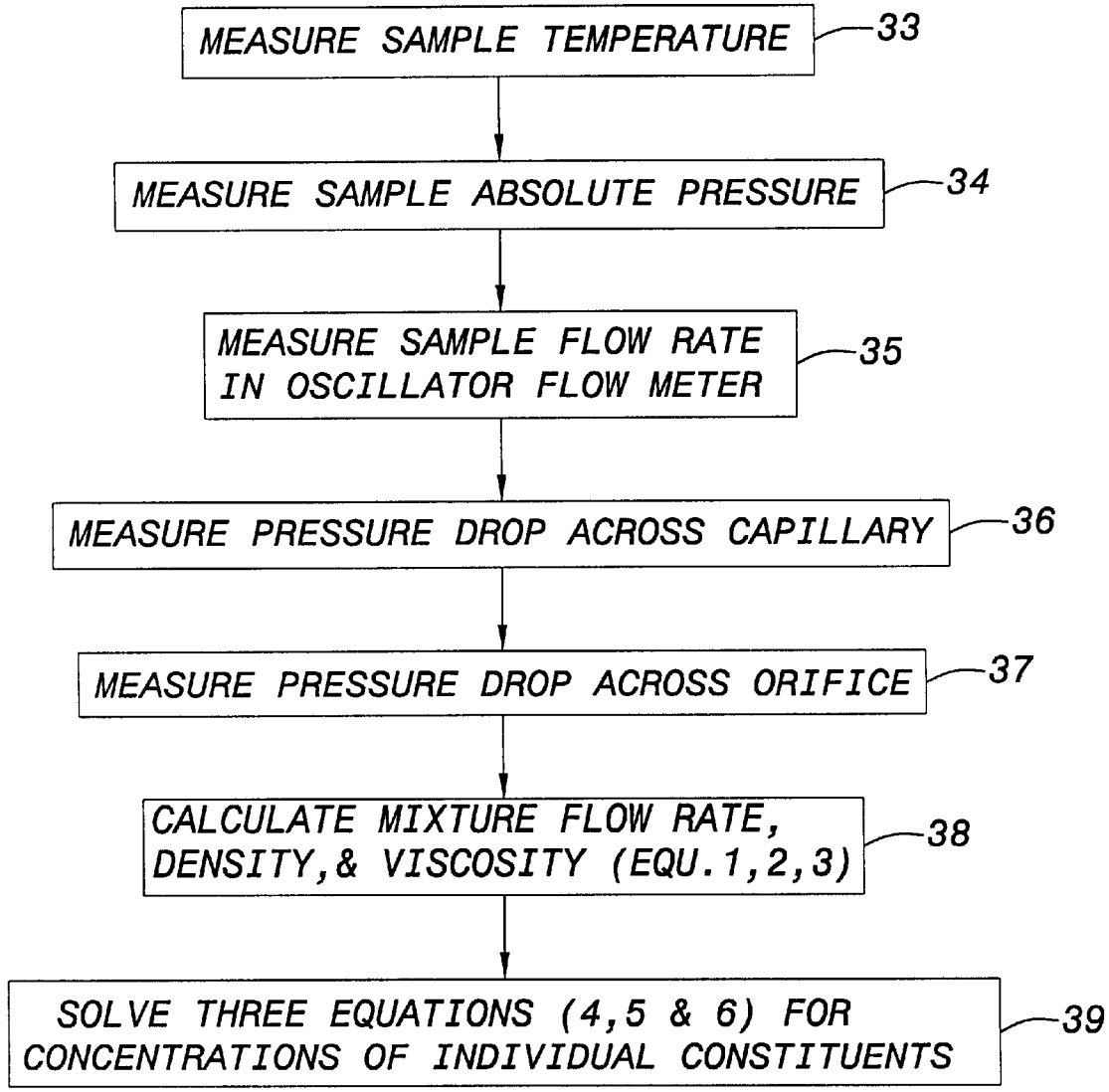
FIG. 5b is a flow chart summarizing the processing steps involved in determining the individual concentrations of the constituent gasses in a mixture of three known gasses.

FIG. 5b is a flow chart summarizing the above-described processing steps (steps 33–39) involved in determining the individual concentrations of the constituent gasses in a mixture of three known gasses.

In another more efficient embodiment, the nozzle of the flowmeter itself is used as an orifice instead of a separate orifice so that the measurement of the pressure drop across flowmeter nozzle serves the same purpose. That is, the fluidic amplifier feedback oscillator serves as both a flowmeter and an orifice.

Figure 5C:
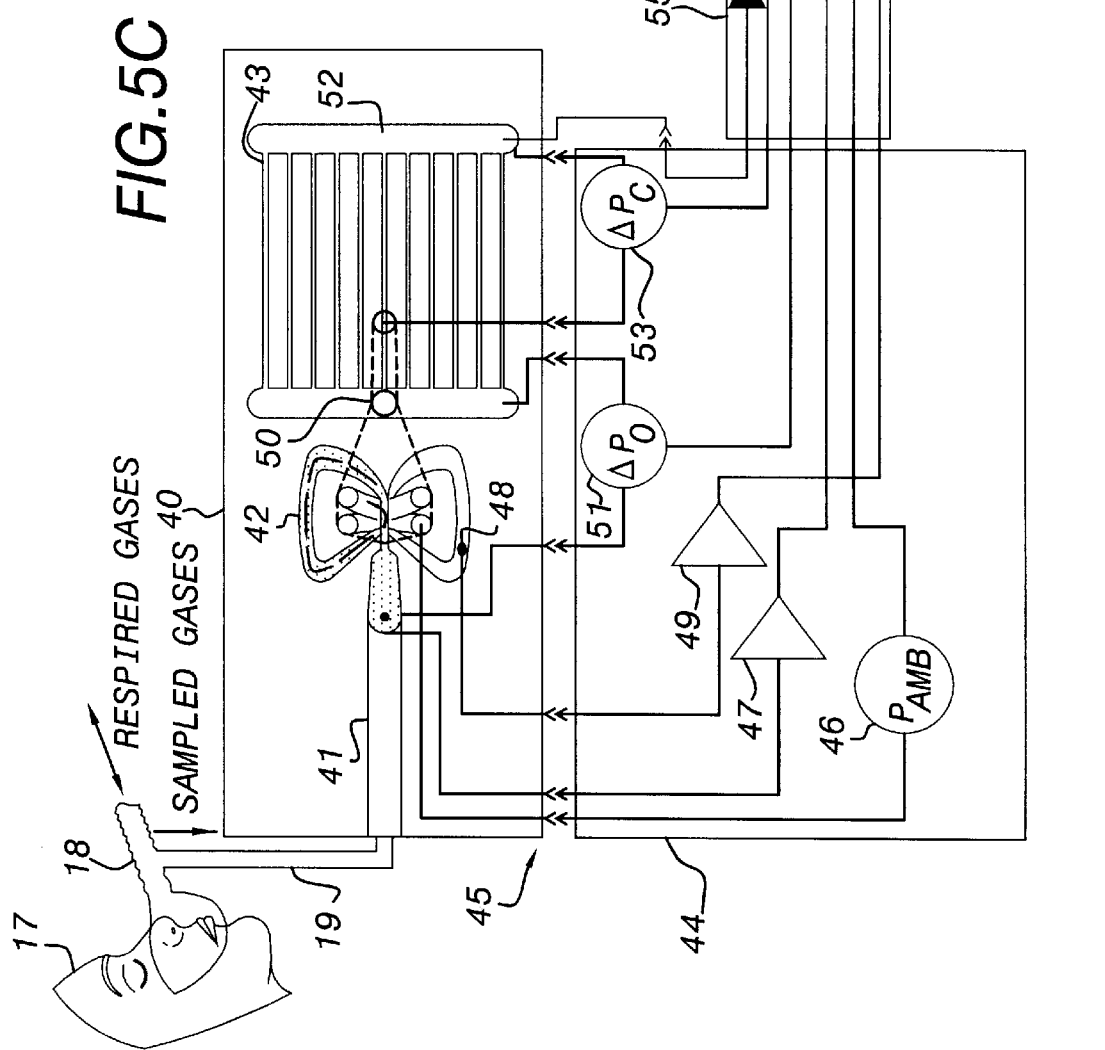
FIG. 5c is a schematic representation of a modular three-gas analyzer including a disposable sensor module.

Preferably, the flowmeter, capillary and orifice are formed on a plate-like module that is disposable after each use to eliminate the possibility of contamination and to simply sterilization of the gas analyzer system. FIG. 5c illustrates a modular three-gas respiration monitor utilizing a disposable sensor module 40. Preferably, disposable sensor module 40 comprises a small, thin, plastic chip containing fluidic sensors. The disposable sensor module 40 receives respired gasses sampled from a side-stream sampling port 19. An on-chip desiccant 41 removes any water vapor that might affect readings, and the desiccated gas mixture flows through a flowmeter 42 and then through a set of substantially parallel capillaries 43. The capillary comprises multiple parallel channels to facilitate accurate manufacture (fabrication errors are thus self-canceling) as well as to provide for a low resistance, thereby minimizing vacuum requirements.

The disposable sensor module 40 is connected to a replaceable transducer module 44 by a separable interface 45. The cost of the replaceable transducer module 44 is low enough to permit it to be discarded in the event of a catastrophic contamination by infected fluids or damage in the field. The transducer module 44 contains the transducers necessary for sensing the temperature and pressures of the gas mixture in the fluidic devices in the disposable sensor module 40. The separable interface 45 conveys electric signals from temperature and microphone sensors, connects pressure transducers to appropriate points in the fluidic sensors, and receives the sample flow exhausted from the set of capillaries 43. The transducer module 44 is connected to a low cost expendable electronics module 54 via a replaceable vacuum line and electrical wire umbilical 55. The expandable electronics are low enough in cost so that they would not constitute a separate budget item but, rather, would be a regularly stocked item.

Prior to entering the oscillator flowmeter 42, the ambient pressure of the gas sample is measured by an absolute pressure transducer 46 on board transducer module 44. The voltage from transducer 46 is transmitted via umbilical 55 to a sample and hold circuit of a multiplexer 56 on board the electronics module 54. An A/D converter 57 converts the analog signals generated by the sample and hold circuit of multiplexer 56 into a digital signal that is supplied to a microprocessor 58.

A temperature sensor provides a voltage proportional to the ambient gas temperature, and the output voltage is amplified by electronic amplifier 47 on board transducer module 44 and transmitted via umbilical 55 to the multiplexer 56, A/D converter 57 and microprocessor 58.

The sample flow rate is then measured in the oscillator flowmeter 42. A microphone 48 picks up the oscillating pressure signals which are amplified by an electronic amplifier 49 on board transducer module 44. The output of amplifier 49 is supplied via umbilical 55 to a frequency counter 59 in electronics module 54. Frequency counter 59 may employ a high-frequency electronic oscillator which is gated by the frequency signal from amplifier 49 to produce a real-time digital frequency measurement which is provided directly to microprocessor 58. This simplified arrangement advantageously eliminates the need for a frequency-to-voltage converter and the need for subsequent A/D conversion of the frequency signal. The flow exiting flowmeter 42 enters into a capillary entrance 50.

In the exemplary embodiment shown in FIG. 5c, the oscillator 42 functions as both the flowmeter and the orifice. Specifically, a differential pressure transducer 51 on board transducer module 44 measures the pressure drop across the oscillator flowmeter (orifice) 42 by measuring the difference between the pressure upstream of the amplifier nozzle at the entrance to the flowmeter oscillator 42 and the pressure downstream in the amplifier vent region at the capillary entrance 50. The output voltage from pressure transducer 51 is transmitted via umbilical 55 to multiplexer 56, A/D converter 57 and then to microprocessor 58 on board electronics module 54.

The structure and operation of the parallel capillary arrangement will now be described. As shown in FIG. 5c, a single capillary entrance 50 and a single capillary exit 52 are connected via a plurality of substantially parallel capillaries 43. Capillary entrance 50 extends longitudinally in a direction substantially perpendicular to the longitudinal direction of the capillaries 43, with each of the capillaries 43 extending from one longitudinal side of entrance 50. Capillary entrance 50 receives the sample gas flow from the output of flowmeter 42 and distributes the flow to the plurality of capillaries 43. Capillary exit 52 extends longitudinally in a direction substantially perpendicular to the longitudinal direction of the capillaries 43, with each of the capillaries terminating on one longitudinal side of the capillary exit 52. A differential pressure transducer 53 on board transducer module 44 measures the pressure drop across all of the capillaries by measuring the difference between the upstream pressure at a point within a capillary and the downstream pressure at the capillary exit 52. The output voltage from pressure transducer 53 is transmitted via umbilical 55 to multiplexer 56, A/D converter 57 and then to microprocessor 58 on board electronics module 96.

The parallel capillary structure provides a number of advantages. Specifically, each individual narrow capillary has a relatively high level of flow resistance, which is desirable for accurately measuring the pressure drop across one of these capillaries and minimizing entrance flow effects. However, the multiple capillaries allow a relatively high overall flow rate to be maintained. That is, in a manner analogous to electrical resistance, while the flow resistance in a single capillary is relatively high, the overall flow resistance is significantly lower due to the parallel arrangement of the capillaries, which collectively allow a much greater flow.

Additionally, by reducing the flow (and consequently the Rayleigh number) in each channel, the parallel capillary arrangement significantly reduces the length over which non-linear entrance effects are felt before the flow becomes fully developed in the capillary. By reducing this entrance effect, the length of the capillary required for an accurate linear pressure measurement relative to flow is reduced.

The parallel capillary arrangement also makes manufacturing repeatability simpler, cheaper and more feasible. Specifically, required manufacturing tolerances are a function of the required accuracy of the pressure measurements, since the dimensions of the capillary are assumed to have certain values (geometric constants) in the computation of viscosity and density (see equation 1). However, with the multiple capillary arrangement, the impact of random variations in the dimensions of individual capillaries diminishes with an increasing number of capillaries. By way of example, in the case of a single capillary with a nominal width of 0.25 mm, in order to ensure that device-to-device differences in air flow resistance are no greater than in the fifth significant digit, the manufacturing tolerances would have to be in the nanometer range. However, since deviations in width occur randomly, the deviations tend to cancel out if sufficient numbers of capillaries are used in parallel. For example, putting two capillaries in parallel reduces the effects of fabrication errors by a factor of ten. Four capillaries in parallel will reduce the effects of fabrication errors by another factor of ten, and eight capillaries in parallel will reduce the effects by yet another factor of ten. Thus, by using eleven capillaries in parallel, as shown in FIG. 5c, the effects of dimensional variations can be reduced by well over three orders of magnitude, providing effective nanometer tolerances (and the manufacturing repeatability associated therewith) with actual tolerances on the order of microns, which are readily achievable with standard precision manufacturing methods such as precision injection molding.

The aforementioned manufacturing repeatability is an important aspect of producing a low-cost device, since it obviates the need for individual unit characterization during manufacturing and eliminates the need for user calibration prior to or during use of the system. Specifically, the aforementioned fabrication tolerances allow the geometric constants used in equations 1–3 to be known a priori or to be characterized during production in the factory. By measuring the pressure-flow (P–Q) characteristics of a single unit using calibration gasses with precisely known properties traceable to primary standards and fitting the known functional relationships to the data, extremely accurate regressions can be used to evaluate the geometric constants which can then be used for other units; thus, geometric characterization of a single unit can obviate the need for individual unit characterization. Given electronic pressure transducer stability and the fact that the equations to be solved are derived from first principles, no user calibration is ever required throughout the lifetime of the system.

While shown in FIG. 5c as being physically parallel, capillaries 43 can be arranged in any convenient manner, provided that they produce parallel flow resistance between a common entrance and a common exit. Thus, as used herein, the term "parallel" connotes parallel air flow resistivity but not necessarily a physically parallel arrangement, while the terms "physically" or "substantially" "parallel" connote the actual physical arrangement of the capillaries.

From capillary exit 52, the sample gas is routed through a gas exhaust passage of separable interface 45 to transducer module 44 and then through umbilical 55 to a vacuum pump 89 located inside the enclosure holding the electronics module 54, from which the gas is exhausted to the atmosphere through an appropriate filtering mechanism.

Microprocessor 58 controls a liquid crystal display 60 which displays medical information derived from the measurements processed by microprocessor 58, including individual concentrations of the gasses of interest of the sample gas mixture.

Referring now to FIG. 6, a perspective view of actual hardware is shown illustrating the small size (shown relative to a coin, i.e., a U.S. quarter dollar), compactness and simplicity of the device which provides a low cost. FIG. 6 shows a stack of fluidic metal laminations held together with screws which may be replaced by diffusion-bonded stack or injection molded assemblies in production devices.

As disclosed in the above-mentioned provisional applications, the above-described three-gas analyzer can be used to determine concentrations of respired anesthesia gasses. In this case, after analysis, the exhaled gasses may be scrubbed of carbon dioxide in a scrubber filter and returned to the anesthesia machine. By way of example, the present invention may be utilized to analyze a set of gas mixtures that are typically encountered in actual anesthesia practice, such as oxygen, $O_2$, carbon dioxide, $CO_2$, and the potent anesthesia agent, halothane, $C_2HBrClF_3$. This gas mixture is one that occurs after a short time (e.g., about 7 minutes) after a patient has expelled all residual dissolved nitrogen and, under a relatively common situation, where the potent anesthetic is administered alone without nitrous oxide (e.g., standard practice is to reduce the concentration of potent anesthetic by providing a high dose of nitrous oxide, $N_2O$, which is thought to mitigate side effects of the potent anesthetic). This simpler mixture is now often used with children and obstetric cases as it is advantageous because the danger of suffocation in nitrous oxide in the event of a loss of oxygen is reduced. The administration of a single anesthesia agent without nitrous oxide, however, is still typically not standard general practice.

Figure 7A:
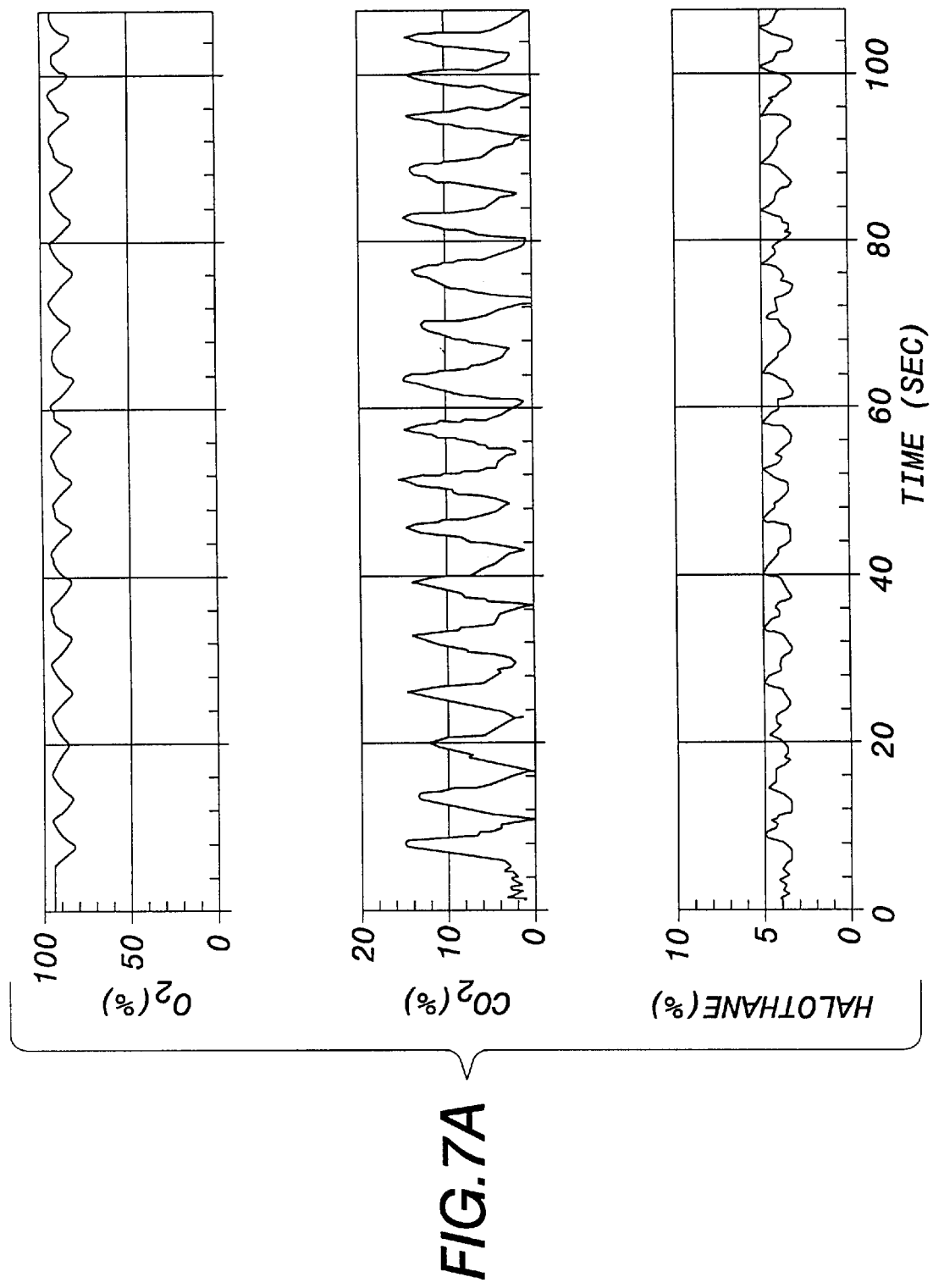
FIG. 7a shows in graphical form actual real time data of the outputs of a three-gas analyzer measuring oxygen, carbon dioxide and halothane (i.e., a potent volatile anesthetic), from a three gas analyzer.

FIG. 7a shows three exemplary real time traces of the concentration histories during simulated respiration of an anesthetic mixture. Respiration is simulated by periodically adding about ten percent carbon dioxide. When $CO_2$ is added, the concentrations of oxygen and halothane decrease (e.g., if the gas was actually respired, the concentration of halothane remains approximately constant because the amount of oxygen and carbon dioxide relative to the halothane is fixed since the oxygen is metabolized into carbon dioxide, that is, only $O_2$ and $CO_2$ are out of phase). Halothane is resolved to about ±0.05% volume concentration. By specifically measuring the physical properties of the mixture, specificity of the individual concentrations is automatically ensured.

Figure 7B:
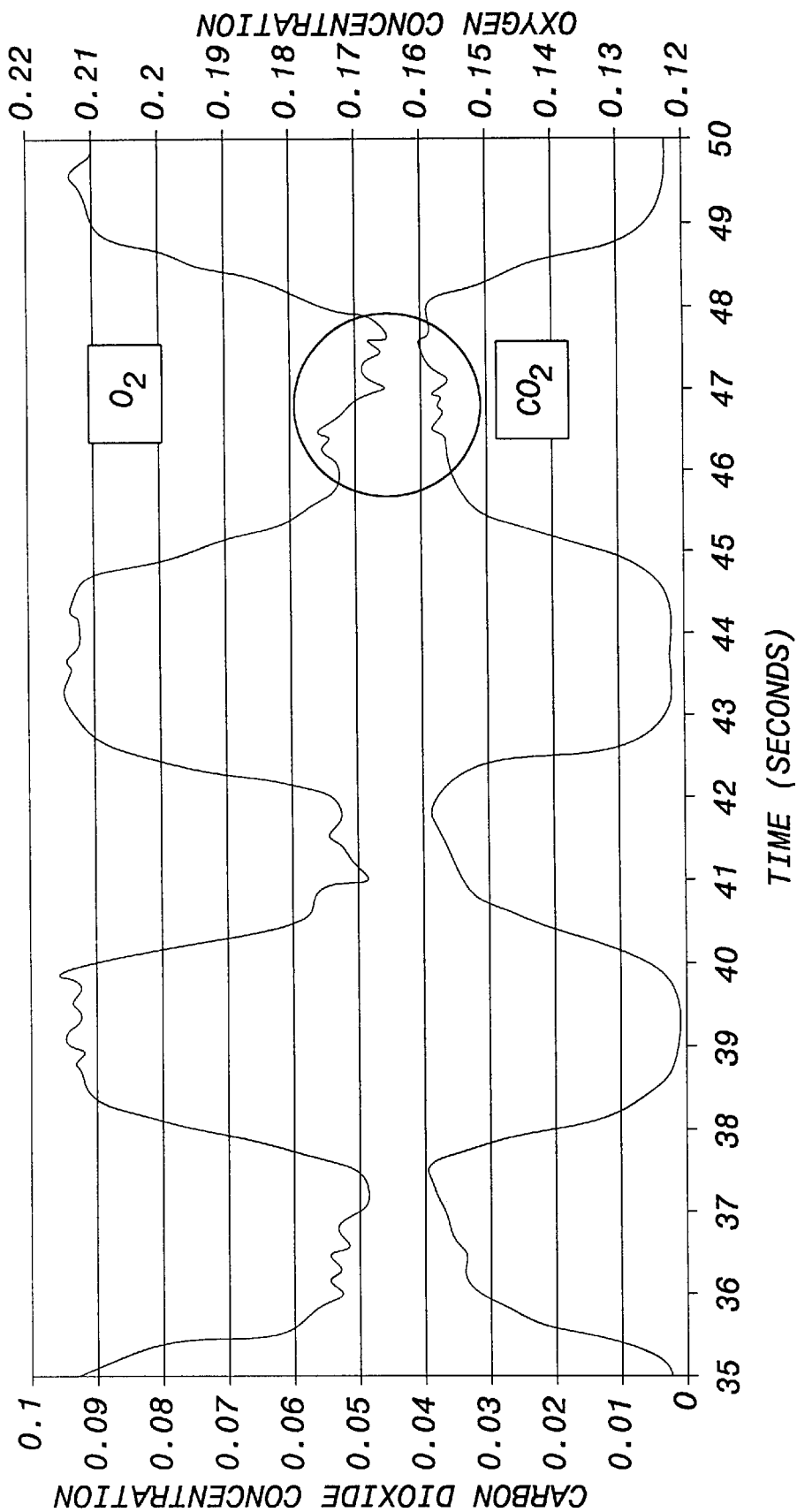
FIG. 7b shows exemplary real time traces of oxygen and carbon dioxide during actual respiration in an air monitoring mode of operation.

FIG. 7b shows exemplary real time traces of oxygen and carbon dioxide during actual respiration of an adult male when the monitoring mode is for air (a three-gas mixture of $O_2$, $CO_2$ and pseudo-nitrogen ($N_2$+Ar+traces)). The typical capnographic trace of $CO_2$ shown a well-defined sharp rise to a plateau with an end-tidal value just preceding inhalation. The noise represents less than 0.5% volume upon concentration. As seen in the circled portion of the traces, irregularities in the traces indicate premature ventricular contractions.

Figure 7C:
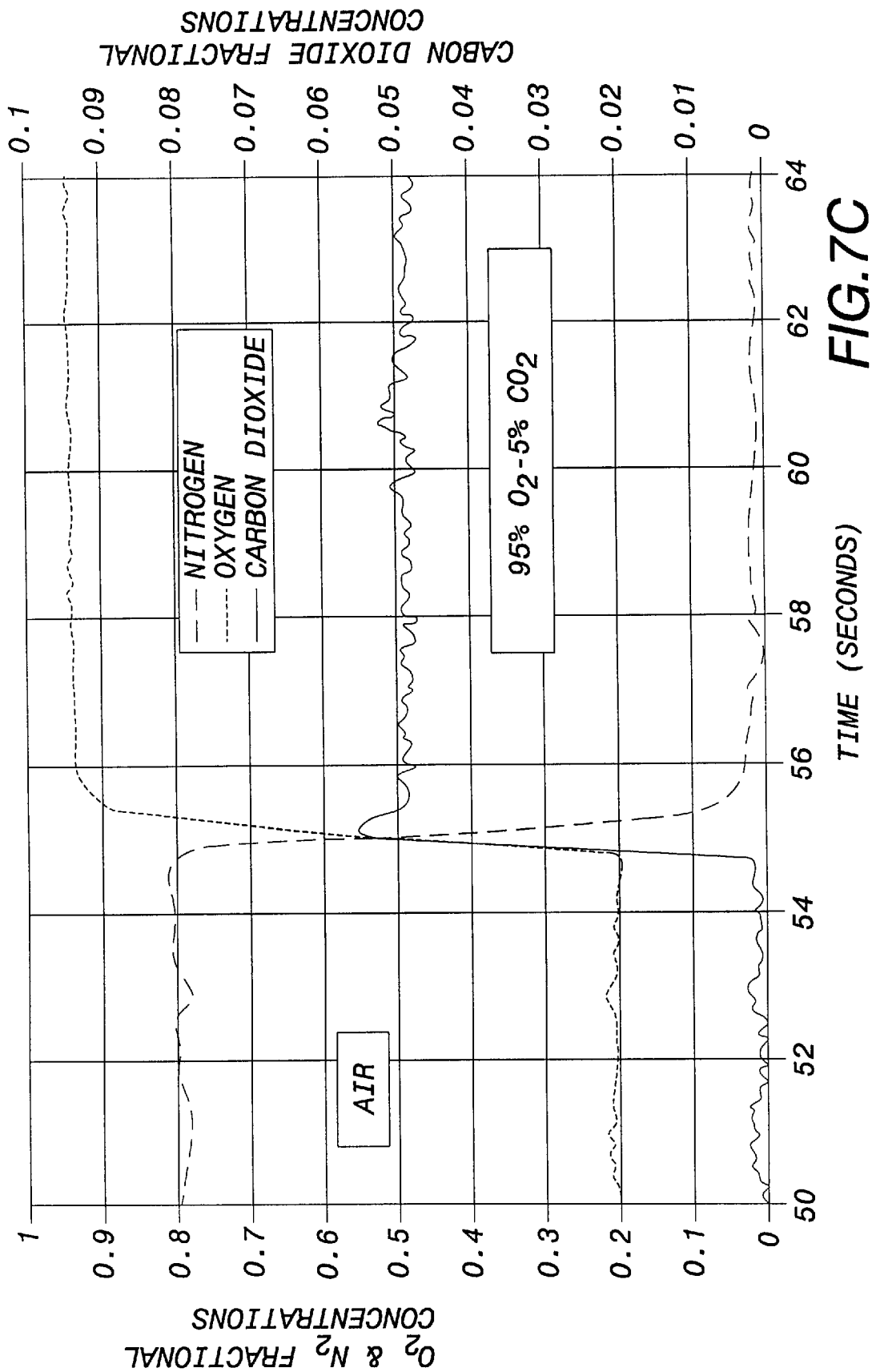
FIG. 7c shows the response of the system of the present invention to a calibration gas composed of 95% $O_2$ and 5% $CO_2$.

FIG. 7c shows the system response to a calibration gas composed of 95% $O_2$ and 5% $CO_2$. This time trace begins with the sensor sampling dry air and initially shows the constituents of air as 79% $N_2$+traces, 21% $O_2$, and approximately 0% $CO_2$, as is expected. When the calibration gas is turned on, the nitrogen concentration goes to zero, the oxygen concentration rises to approximately 95%, and the $CO_2$ concentration rises to almost exactly 5%. Noteworthy here is the accuracy and resolution of $CO_2$. The accuracy is ±0.25 volume % as shown by the average value of $CO_2$, and the resolution is also ±0.25 volume % as demonstrated by the noise of the measurement. It is instructive to note that the accuracy and resolution is the same for all three gasses measured. This is because of the way the concentrations are reconciled by the constitutive equation (concentrations sum to one). This has a very important implication on the measured values of $O_2$. Since the accuracy is independent of concentration value, this measurement technique gives rise to significantly better accuracy at high concentration levels than conventional sensors which normally have an accuracy which is a fixed percentage of the concentration. Thus, a conventional $O_2$ sensor that provides readings accurate to ±2% of reading may be quite accurate at low concentration levels (at 10% concentration the accuracy would be 0.2 volume percent) but less accurate at high concentration levels (at 95% concentration, the accuracy is 2 volume percent). In contrast, the device of the present invention maintains its ±0.1 volume percent accuracy over the entire range of concentrations, e.g., 95±0.25% and 10±0.25%.

In order to determine the individual concentrations of four gas constituents in a mixture of four gasses, an additional property, independent of density and viscosity, must be measured. The specific heat at constant pressure, $c_p$, is one such property. It is a unique gas property independent of density and viscosity and is normally determined by measuring the speed of sound in the gas. From the kinetic theory of gasses, the speed of sound, a, is defined as:

$$a = [yR_0T/M]^{1/2} \qquad (7)$$

where $R_o$ is the universal gas constant, T is the absolute temperature, M is the molecular weight and y is the ratio of specific heats, $c_p/c_v$, $c_v$ being the specific heat at a constant volume. Molecular weight, being directly proportional to density, is available from the sensor densitometer function. The specific heats $c_p$ and $c_v$ are related by the gas constant and molecular weight:

$$c_p = c_v + R_o/M \qquad (7a)$$

From equations (7) and (7a), the following expression for $c_p$ can be derived:

$$c_p = \frac{1}{\dfrac{M}{R_0} - \dfrac{T}{a^2}} \qquad (8)$$

Since density ρ is related to molecular weight M and absolute pressure $p_{amb}$ (terms that are measured), equation (8) can be rewritten as:

$$c_p = 1/[T(\rho_{mix}/P_{amb} - 1/a^2)] \qquad (8a)$$

As noted previously in the design of the fluidic flowmeter oscillator, the frequency of a fluidic feedback oscillator depends on the transit time of the fluid from the input ports to the output ports of the interaction region, and the acoustic feedback time from the output ports back to the input ports. In general, frequency $f_{sonic}$ of the sonic oscillator and the flow rate Q are related to the speed of sound by:

$$a = 2L_{fbA}/[1/f_{sonic} - 4x_{spA}b_A h_A/Q] \qquad (9)$$

where $L_{fbA}$ is the path length of the feedback lines, $x_{spA}$ is path length from the input ports to the output ports of the oscillator interaction region, and $b_A$ and $h_A$ are the oscillator supply nozzle width and height, respectively. By making the path length of the feedback lines long, the acoustic delay becomes the dominant term relative to the transit time. In general, therefore, if the frequency f of a sonic oscillator is proportional only to the speed of sound, $$a = kf_{sonic},$$

then the ratio of specific heats (and consequently the specific heat, $c_p$) of a mixture can be determined from the relationship, $$Y_{mix} = [kf_{sonic}]^2 M_{mix}/R_o T \qquad (10)$$

Figure 8:
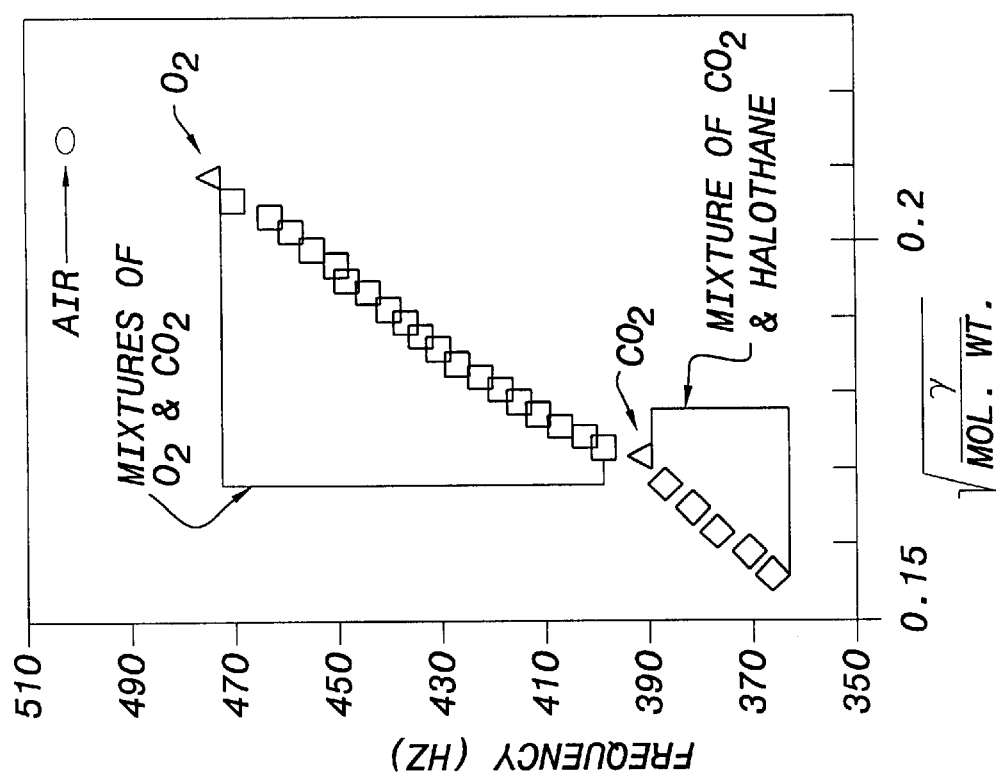
FIG. 8 shows data in graphical form of frequency versus the square-root of ratio of specific heats to molecular weight for a long feedback line fluidic oscillator.

FIG. 8 shows a plot of the frequency of an early DRT model 51009 sonic oscillator with approximately ten inch long feedback lines as a function of the square root of y/M. The data is roughly linear. The data points corresponding to different ratios of y and molecular weights are obtained by operating the oscillator with various gas mixtures of known concentrations.

The relationship between the concentrations of the various gasses and the specific heat is a similarly simple linear relationship as was the case with density and molecular weight. The specific heats of the mixture are related to the individual component specific heats by weight fraction of each component; thus, $$c_{p\,mix} = C_1 M_1 c_1 + C_2 M_2 c_{p2} + \ldots \qquad (11)$$

or $$c_{p\,mix} = \sum_i^N C_i M_i c_{pi} \qquad (12)$$

and $$c_{v\,mix} = C_1 M_1 c_{v1} + C_2 M_2 c_{v2} + \ldots \qquad (13)$$

or $$c_{vmix} = \sum_i^N C_i M_i c_{vi} \qquad (14)$$

Thus, by measuring the three properties of density, viscosity and a specific heat of a mixture of four gasses, four independent equations (equations 4, 5, 6 and 12 or 14) can be solved for the four unknown concentrations of the individual four gasses.

In the context of anesthesia gas administration, determination of the concentrations of five gasses can be achieved without measuring an additional independent property (i.e., by measuring only these three properties) by adding an additional piece of information to solve for the fifth gas. Five-gas mixtures typify modem anesthesia administration. The five gasses are typically: nitrogen, oxygen, carbon dioxide, nitrous oxide, and a potent, volatile anesthetic agent. Nitrogen is the primary component of air and is typically present in respired gasses, and even when the administered gasses are free of nitrogen (which is typically the case during administration of anesthesia) nitrogen remains present as a residual for several minutes from previously having breathed air. The ability to measure nitrogen is a major safety benefit during administration of anesthesia, since a sudden small presence of nitrogen may indicate an air embolism, and a large presence may indicate a loss of breathing circuit integrity (e.g., a leak in the system).

Measurement of the concentration of oxygen, which is administered or present in air, provides redundancy to the breathing circuit $O_2$ sensor (e.g., a Clark electrode) and eliminates any pulse oximeter CO ambiguity. Measurement of the concentration of $CO_2$, which is a product of the body's metabolic processes, can be combined with the oxygen measurement to provide a respiratory quotient and to validate respiration.

Nitrous oxide is typically administered in combination with a volatile anesthetic agent, and measurement of its concentration prevents overdosing and asphyxiation. Volatile halogenated anesthetic agents are administered to induce anesthesia and include: halothane, desflurane, sevoflurane, enflurane, and isoflurane. Monitoring of two volatile potent anesthetic agents simultaneously when one is discontinued and a new one is started is possible after the nitrogen disappears some 7–15 minutes into most normal procedures. This capability can be provided by allowing the user to identify the known makeup of the five gasses, that is, when nitrogen is no longer physiologically present (i.e., when the system shows that it is no longer present), and only four gasses remain. At that point another, different gas component (e.g., helium used during laser surgery or a second anesthetic agent), can be additionally considered and/or measured.

Importantly, however, carbon dioxide and nitrous oxide have almost exactly the same molecular weight, density and viscosity and very similar specific heats. Thus, these two gasses, typically present in respired anesthesia gasses, cannot readily be distinguished by these properties. Given sufficient pressure transducer and flow sensor resolution, these two gasses can be resolved; however, from a practical aspect, resolution would have to be improved by an order of magnitude from the current state-of-the-art. However, anesthesia machines typically remove carbon dioxide from the stream of air that is inspired by the patient under anesthesia; thus, the concentration of carbon dioxide in the inspired gasses is known to be zero. This fact can be used to extend the capabilities of a four gas analyzer to determine the concentrations of five gasses in a typical mixture of anesthesia gasses.

Specifically, for purposes of solving the four equations relating properties of the mixture to individual gas concentrations, carbon dioxide and nitrous oxide are considered to be a single gas, and it is assumed that their properties cannot be distinguished and are the same. Thus, for example, equations (4), (5), (6) and (12) are solved for the concentrations of oxygen, nitrogen, a potent anesthetic gas, and the combination of carbon dioxide and nitrous oxide. The individual concentrations of nitrous oxide and carbon dioxide can then be determined in the following manner. The combined concentration of nitrous oxide and carbon dioxide varies cyclically with respiration, as the concentration of carbon dioxide varies from near zero in the inspired gasses to a maximum during exhalation. Thus, the minimum combined concentration in each cycle can be assumed to be the concentration of nitrous oxide, while the concentration of carbon dioxide can be assumed to be the difference between the combined carbon dioxide-nitrous oxide concentration (which is varying throughout each respiration cycle) and the most recent minimum combined concentration (i.e., the nitrous oxide concentration). According to this approach, the carbon dioxide concentration is computed and updated throughout each cycle (as is the concentration of oxygen, nitrogen and the anesthetic agent), while the nitrous oxide concentration is updated once during each respiration cycle.

Figure 9A:
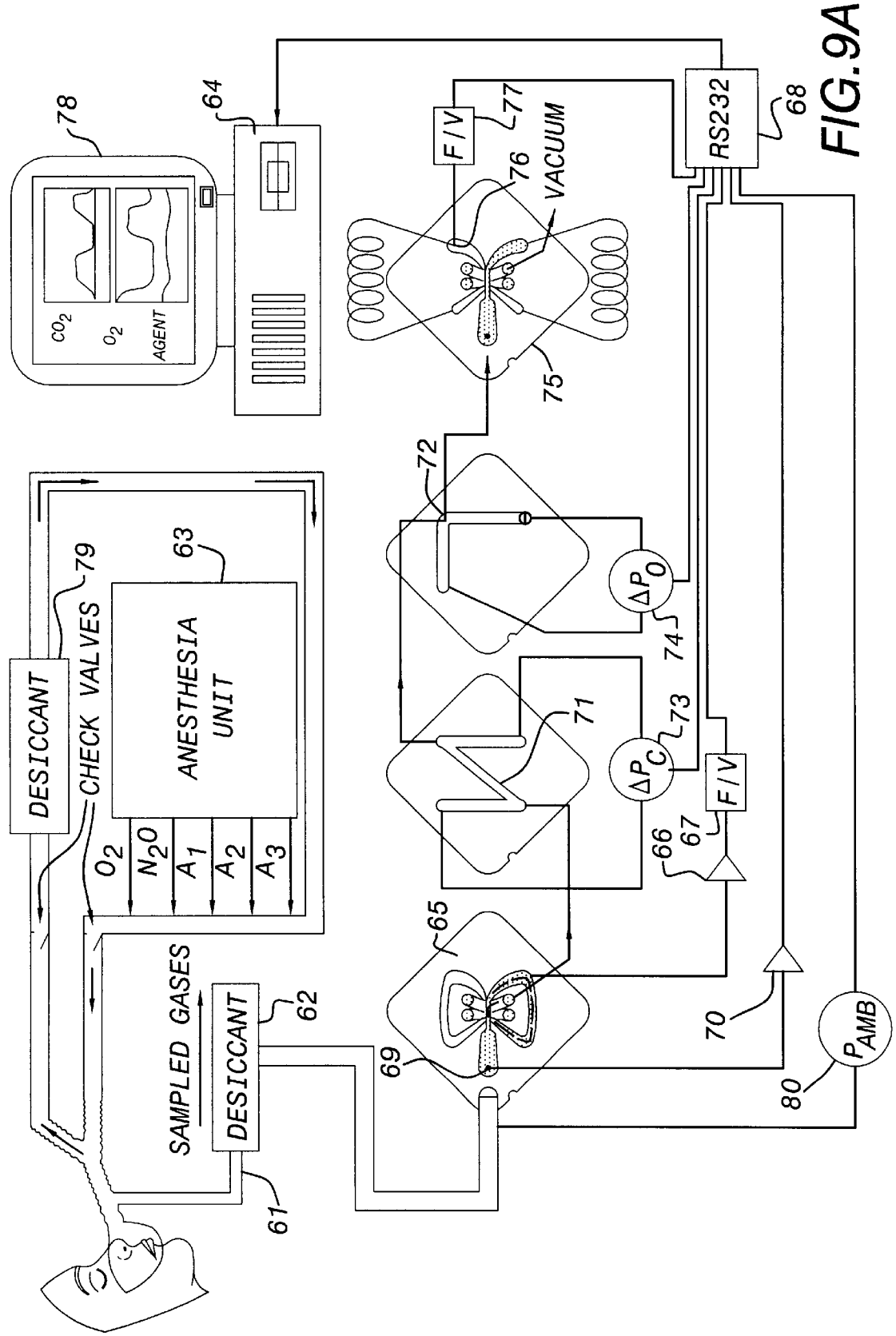
FIG. 9a is a schematic representation of a four-gas analyzer according to the present invention.
Figure 9B:
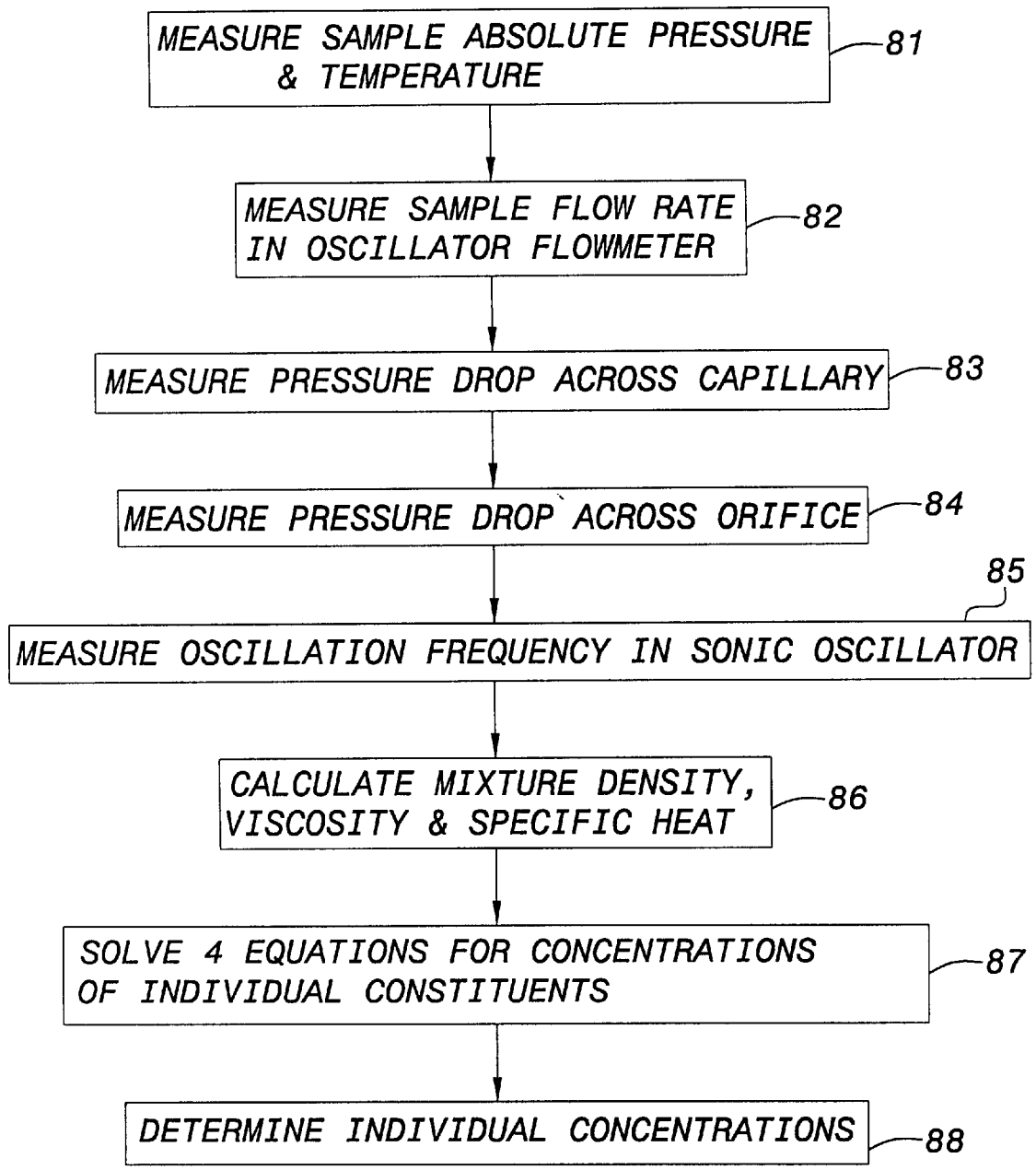
FIG. 9b is a flow chart summarizing the processing steps involved in determining the individual concentrations of the constituent gasses in a mixture of five known gasses.

Referring now to FIG. 9a, a five-gas analyzer is shown. This analyzer is designed to generally be utilized in operating rooms, outpatient surgery centers or any facility that uses anesthetic gasses and/or sedation, to analyze concentrations of multiple respired anesthetic gasses simultaneously. FIG. 9b is a flow chart illustrating the processing steps involved in determining the individual concentrations of the constituent gasses in a mixture of five known gasses.

As before in the three-gas analyzer shown in FIG. 5a, the respired gasses are side-stream sampled through a sampling port 61 and passed through a desiccant 62 to remove all traces of water and water vapor. The majority of the respired gasses are passed through a soda lime filter and desiccant 79 to remove carbon dioxide and water vapor and then recirculated through the breathing circuit. The anesthetic gasses (e.g., nitrous oxide and a volatile potent anesthetic) are supplied from an anesthesia machine 63 to the inspired gasses. Since many anesthesia machines permit only a single potent anesthetic to be dispensed, the opening of an interlocked valve may be electronically monitored and a signal identifying which anesthetic is being dispensed is transmitted to a microprocessor 64 via an electrical connection (not shown) so that the appropriate gas parameters are used in the equations solving for the concentrations.

Prior to entering the oscillator flowmeter 65, the ambient pressure of the sample is, measured (step 81) by a pressure sensor 80 and directed to microprocessor 64 via a multiplexed RS232 port 68. Temperature sensor 69 within flowmeter 65 provides a voltage proportional to the ambient gas temperature, which is amplified by electronic amplifier 70 and directed to microprocessor 64 via RS232 port 68.

The sampled gas then passes through the flowmeter 65 (step 82) and generates a voltage at a frequency proportional to flow which is amplified by electronic amplifier 66, and the frequency is converted to a voltage proportional to the frequency in F/V converter 67. This voltage is passed to the microprocessor 64 via RS232 port 68. As with the three-gas analyzer, the sampled flow passes through a viscosity sensing capillary 71 (step 83) and a density sensing orifice 72 (step 84). Differential pressures across the capillary 71 and orifice 72 are measured by pressure transducers 73 and 74, respectively. The respective transducer output voltages are transmitted to microprocessor 64 via RS232 port 68. The sampled gas continues through the sonic oscillator 75 (step 85) which generates an acoustic frequency proportional to the square root of the ratio of specific heats and inversely proportional to the square root of the molecular weight. Microphone 76 (or a pair of microphones as in the three-gas analyzer) picks up this frequency which is fed into a frequency-to-voltage (F/V) converter 77 which provides a voltage proportional to the square root of the ratio of specific heats γ, divided by molecular weight. This voltage is sent to microprocessor 64 via RS232 port 68. The sampled gas is finally exhausted to a vacuum source (not shown).

In step 86, using the assumption that carbon dioxide and nitrous oxide are a single constituent, the microprocessor 64 solves the four simultaneous equations, three involving the three measured properties, equations (4), (5), and (12), and the fourth being the constitutive equation, equation (6), that requires that the sum of the concentrations be unity.

$$\rho_{mix} = \Sigma \rho_i C_i \tag{4}$$

$$\mu_{mix} = \Sigma \mu_i [1 + (1/C_i) \Sigma C_j \phi_{ij}], j \neq i \tag{5}$$

$$C_{pmix} = \sum_i^4 C_i M_i c_{pi} \tag{12}$$

$$\Sigma C_i = 1 \tag{6}$$

In step 88, the individual concentrations of carbon dioxide and nitrous oxide are then determined by microprocessor 64 in the previously-described manner. The resultant concentrations and any other derived outputs may be presented on display 78 which is controlled by microprocessor 64.

In most recirculating anesthesia administration systems, exhaled gasses are scrubbed of carbon dioxide in a scrubber filter (not shown) and returned to the anesthesia machine 63.

Preferably, the gas analysis is performed by a flowmeter oscillator (also serving as an orifice), a capillary and a sonic oscillator formed on a plate-like single chip module that is disposable after each use to eliminate the possibility of contamination and to simplify sterilization of the gas analyzer system.

Figure 9C:
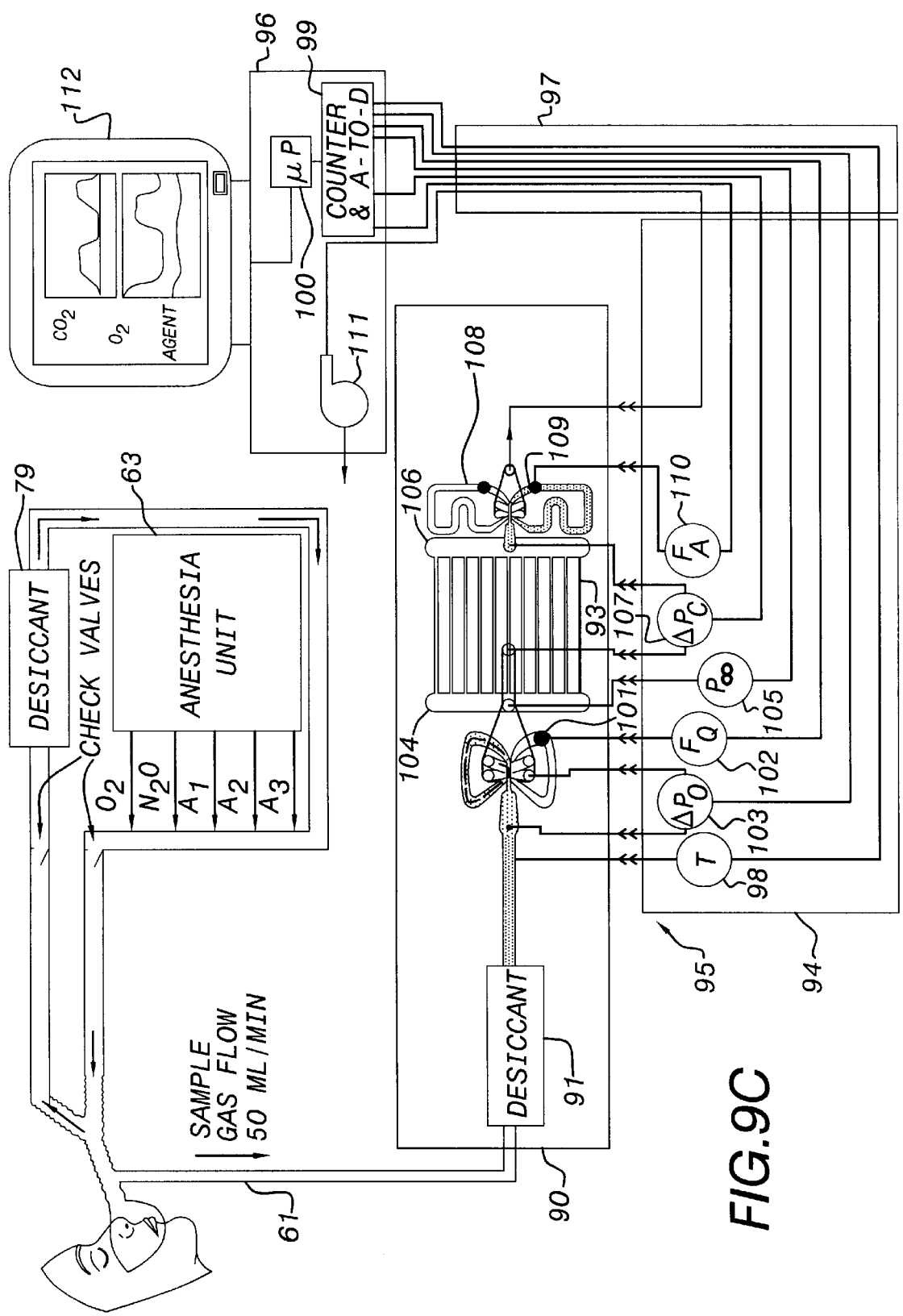
FIG. 9c is a schematic representation of a four-gas analyzer including a disposable sensor module.

FIG. 9c illustrates a modular four-gas (five-gas for anesthesia administration) respiration monitor utilizing a disposable sensor module 90. Preferably, disposable sensor module 90 comprises a small, thin, plastic lamination containing the fluidic sensors. The disposable sensor module 90 receives respired gasses sampled from a side-stream sampling port 61. An on-board desiccant 91 removes any water vapor that might affect readings, and the desiccated gas mixture flows through a flowmeter oscillator 92 and then through a set of parallel capillaries 93.

The disposable sensor module 90 is connected to a replaceable transducer module 94 by a separable interface 95. The cost of the replaceable transducer module 94 is low enough to permit discarding in the event of a catastrophic contamination by infected fluids or damage in the field. The transducer module 94 contains the transducers and amplifiers necessary for sensing the characteristics of the gas mixture in the fluidic devices on board the disposable sensor module 90. The separable interface 95 conveys electric signals from temperature and microphone sensors, connects pressure transducers to appropriate points in the fluidic sensors, and receives the sample flow exhausted from the sonic oscillator 108. The transducer module 94 is connected to an electronic computational module 96 via a replaceable vacuum line and electrical cable umbilical 97.

Prior to the sample gas entering the oscillator flowmeter 92, a temperature sensor measures the sample gas temperature at the flowmeter entrance and provides a voltage proportional to the measured temperature. The output voltage is amplified by electronic amplifier 98 on board transducer module 94, and the amplified voltage is transmitted via umbilical 97 to an AID converter 99 which converts the signal into a digital signal that is supplied to a microprocessor 100.

The sample flow rate is then measured in the oscillator flowmeter 92. A microphone picks up the oscillating pressure signals which are amplified by an electronic amplifier 102 on board transducer module 94. The output of amplifier 102 is supplied via umbilical 97 to a frequency counter 99 in electronics module 96 which provides a real-time digital frequency measurement directly to microprocessor 100.

In the exemplary embodiment shown in FIG. 9c, the oscillator flowmeter 92 functions as both the flowmeter and the orifice. Specifically, a differential pressure transducer 103 on board transducer module 94 measures the pressure drop across the oscillator flowmeter (orifice) 92 by measuring the difference between the pressure upstream of the amplifier nozzle at the entrance to the flowmeter oscillator 92 and the pressure downstream of the nozzle at output of oscillator 92. The output voltage from pressure transducer 103 is transmitted via umbilical 97 to A/D converter 99 and then to microprocessor 100 on board electronics module 96. Alternatively, sonic oscillator 108 supply nozzle may be used as the densitometer orifice. This may be advantageous, as the pressure drop in generally higher, and a less sensitive, lower cost differential pressure transducer may be used to measure the pressure drop.

The flow exiting flowmeter 92 enters into a capillary entrance 104. The absolute pressure of the gas sample at the capillary entrance 104 is measured by an absolute pressure transducer 105 mounted in the transducer module 94. The voltage from transducer 105 is transmitted via umbilical 97 to A/D converter 99 and then to microprocessor 100 in the electronics module 96.

As shown in FIG. 9c, a single capillary entrance 104 and a single capillary exit 106 are connected via a plurality of substantially parallel capillaries 93. The structure and operation of the parallel capillary arrangement are the same as those described in relation to FIG. 5c. A differential pressure transducer 107 in transducer module 94 measures the pressure drop across one of the capillaries 93 by measuring the difference between the upstream pressure at a point within the capillary 93 and the downstream pressure at the capillary exit 106. The output voltage from pressure transducer 107 is transmitted via umbilical 97 to A/D converter 99 and then to microprocessor 100 on board electronics module 96.

The sampled gas continues from the capillary exit 106 through sonic oscillator 108 which generates an acoustic frequency proportional to the square root of the ratio of specific heats and inversely proportional to the square root of the molecular weight. Microphone 109 picks up the oscillating pressure signals (i.e., the acoustic frequency) which are amplified by an electronic amplifier 110 in transducer module 94. The output of amplifier 110 is supplied via umbilical 97 to a flow counter 99 on board electronics module 96, which produces a digital frequency signal that is provided to microprocessor 100.

From the exit of sonic oscillator 108, the sample gas is routed through a gas exhaust passage of separable interface 95 to transducer module 94 and then through umbilical 97 to a vacuum pump 111 on board electronics module 96, which exhausts the sample gas.

Microprocessor 100 controls a display 112 which displays medical information derived from the measurements processed by microprocessor 100, including individual concentrations of the constituent gasses of the sample gas mixture.

Figure 10:
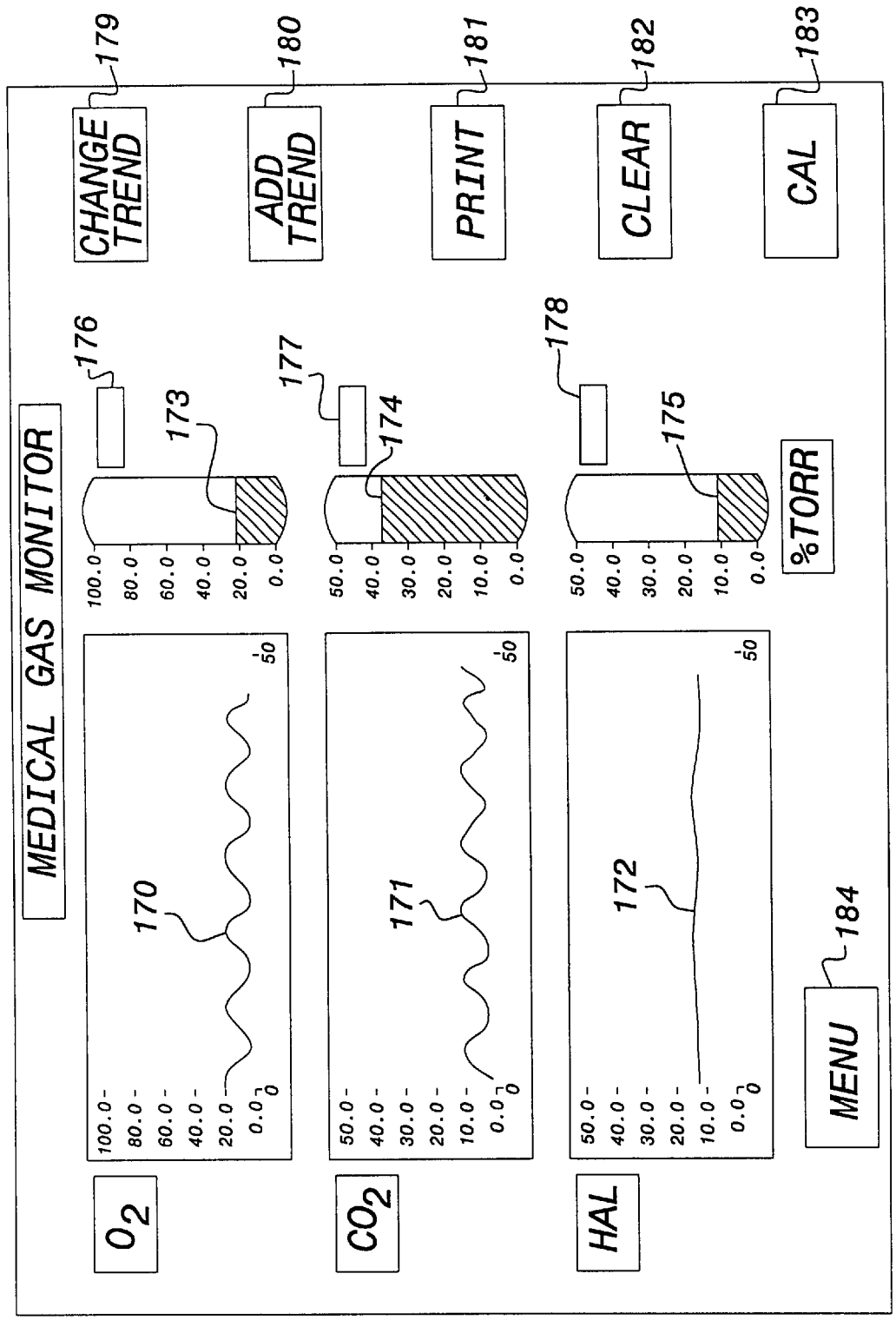
FIG. 10 is a schematic illustration of an exemplary visual output from a virtual instrumentation package.

Referring now to FIG. 10, an exemplary virtual instrumentation screen output is shown. Three displays of real time traces of oxygen concentration 170, carbon dioxide concentration 171 and halothane (i.e., potent anesthetic) concentration 172, are shown (although the number and orientation of traces may of course be adjusted as desired). The instantaneous value of the concentrations are also shown as vertical bars 173, 174, and 175, and also as numeric values 176, 177 and 178. A variety of visual display options can be made available which are illustrated by "Change Trend" 179, "Add Trend" 180, "Print" 181, "Clear" 182, "Cal" (i.e., calculate) 183, and "Menu" 184. It is to be understood that many different screen formats for the data outputs may be utilized and that this one is merely exemplary.

By the addition of a sensor capable of measuring a fourth independent property of a mixture, the system can be extended to determine the concentrations of five gasses in the general case, and a six-gas mixture in the case of anesthetic gasses, where the individual concentrations of carbon dioxide and nitrous oxide are determined in the previously-described manner. Six-gas mixtures occur when water vapor is not removed, or when air is used as the anesthesia carrier. Air additionally introduces argon at about one percent concentration to the gas mixture. The presence of the inert gas argon, however, may be treated as a known constant concentration, in which case properties need be measured. The other trace gasses are in such small concentrations that they do not materially affect the bulk properties of the overall mixture to a discernable amount within the desired clinical accuracy of the system. Water vapor normally occurs at 100% humidity, if not desiccated, and under certain circumstances may also be treated as a known fixed constituent. Removal of water vapor is desirous, however, as it may condense in the fluid passages thereby changing the fluid resistance properties and thus affecting output readings. Operation of the system at elevated temperature to avoid condensation would require a separate heater which, from an energy consumption stand point, is not desirable.

To further reduce costs, special purpose digital signal processing electronics can be used (rather than a general purpose personal computer), and the use of virtual instrumentation techniques with a color display provides outputs in a format that physicians are familiar with, similar to the ubiquitous hospital vital signs monitors. Touch-screen virtual knobs and dials may provide the user with instant and user-friendly reconfiguration capabilities to adjust the output format to one with which a particular user is most comfortable.

The gas concentration monitoring system of the present invention requires no user calibration or maintenance and may be integrated into existing monitoring systems. For example, the sensors shown in FIGS. 5a/5c or FIGS. 9a/9c can be added along the same flow path as other sensors or can be added in a separate flow path. Importantly, the concentration measurements of the other sensors must be provided to the microprocessor along with the measured properties of the mixture in order to solve for the unknown gas concentrations.

Low cost is one of the main attributes of the present invention. Cost for a full-function, four-gas, fluidic multiple medical gas monitor, is determined by the low cost (about $2.00) of the injection molded fluidic circuit and the low cost (about $10.00 each), high accuracy pressure transducers. Since Viscosity, density and specific heat are affected by temperature, ambient temperature measurement is required to maintain accuracy. The temperature sensors described above may be implemented by a simple, ultra low cost electronic temperature sensor, as exemplified by the previously-mentioned Analog Devices AD590 device (at a cost of about $3.00), to provide the required accurate temperature input to the computational processor.

One of the important advantages of the present invention is the ability to simultaneously determine the individual concentrations of N gasses in a mixture of N known gasses by using inexpensive sensors to measure properties of the mixture as a whole and by solving N independent equations relating to the properties of the mixture. Although the above examples describe the invention with three to five gasses, the invention is not limited to the determination of concentrations of only five gasses. If additional properties of the mixture can be independently measured by any means and related to unknown concentrations, concentrations of additional gasses can be determined. In general, if N-1 independent properties of the mixture of gasses can be measured, then N equations can be developed and solved for N gas concentrations (the Nth equation being the constitutive equation (6)).

Other independent thermodynamic properties include, but are not limited to: heats of formation and critical temperature. It should be noted that properties such as thermal conductivity are dependent on specific heat and viscosity and hence are not independent. Other physical properties such as refractive index and absorptivity may also be useful.

Further, while fluidic measurement of the properties of a gas mixture offers a low-cost alternative to more expensive conventional sensors, the principles of the present invention can be extended to include any device which measures properties of the mixture as a whole or concentrations of individual gasses. For example, assume that a particular sensor is capable of determining the concentration of oxygen in a mixture of gasses. The information provided by this separate sensor (i.e., the oxygen concentration) is, in effect, an equation relating to a gas concentration, which equation can be used to solve other equations relating to gas concentrations. Thus, if the oxygen concentration measurement is supplied to the microprocessor 64 in FIG. 9a along with the fluidically measured properties, the concentrations of six gasses in a six gas mixture can be determined (i.e., the oxygen concentration and the concentration of any other five known gasses).

Importantly, fluidic and thermodynamic measurements can be used to determine the unknown gas concentrations in the mixture, regardless of what these gasses are, provided that the identity of the gasses is known and that each gas is distinguishable from all others by at least one of the measured properties. For example, it is desirable to be able to monitor the concentration of nitrogen in a mixture of exhaled gasses while a patient is being anesthetized. During the initial minutes during administration of anesthesia, nitrogen is present in the exhaled gasses, as nitrogen is liberated from lipids and fatty tissues. After approximately ten minutes, nitrogen is not normally present in a significant amount. A leak or break in a supply line would result in the continued presence of nitrogen in the exhaled gasses and can be detected by determining the concentration of nitrogen. However, nitrogen concentrations cannot be measured with conventional IR techniques; thus, more expensive techniques, such as mass spectroscopy typically have been required when it is desirous to determine nitrogen concentrations. According to the present invention, nitrogen concentration can be measured in a three gas mixture by measuring two gas properties and in a five gas mixture (during anesthesia administration) by measuring three gas properties. Further, with the addition of M other sensors which respectively measure the concentrations of M individual gasses, the nitrogen concentration can be measured in a mixture of M+5 gasses, where three gas mixture properties have been measured. Thus, for example, two sensors which measure the concentrations of two gasses can be combined with the three-property measurement device shown in FIGS. 9a/9c to determine the concentration of seven gasses (e.g. nitrogen, oxygen, water vapor, carbon dioxide, nitrous oxide and two anesthesia agents) in real time at very low cost.

More generally, in accordance with the present invention, the capabilities of an existing sensor system for measuring M gas concentrations can be extended to measure N additional gas concentrations by measuring N-1 properties of the gas mixture as a whole, regardless of what the gasses are, provided the identity of the gasses is known. Knowledge of the individual concentrations of certain gasses in the mixture reduces the number of unknowns; thus, N unknown individual concentrations in a mixture of N+M fluids can be determined by solving N equations, where individual concentrations of M fluids are known or determined by other means. For example, many existing anesthesia machines capable of measuring five gasses cannot measure the concentrations of nitrogen, carbon monoxide and helium. By augmenting such a five-gas monitor with the fluidic sensors shown in FIGS. 5a/5c, concentrations of these additional gasses can be measured with little additional expense.

In accordance with another embodiment, the fluidic sensors of the present invention can be used to determine or verify the identity of a gas flowing from a source. Specifically, the identity of a single, unknown gas can be determined by fluidically measuring properties of the gas, such as density and viscosity, and comparing the measured values to known properties of a gas. The identity of the unknown gas can be verified or determined when the fluidically measured values match those of a known gas.

Figure 11A:
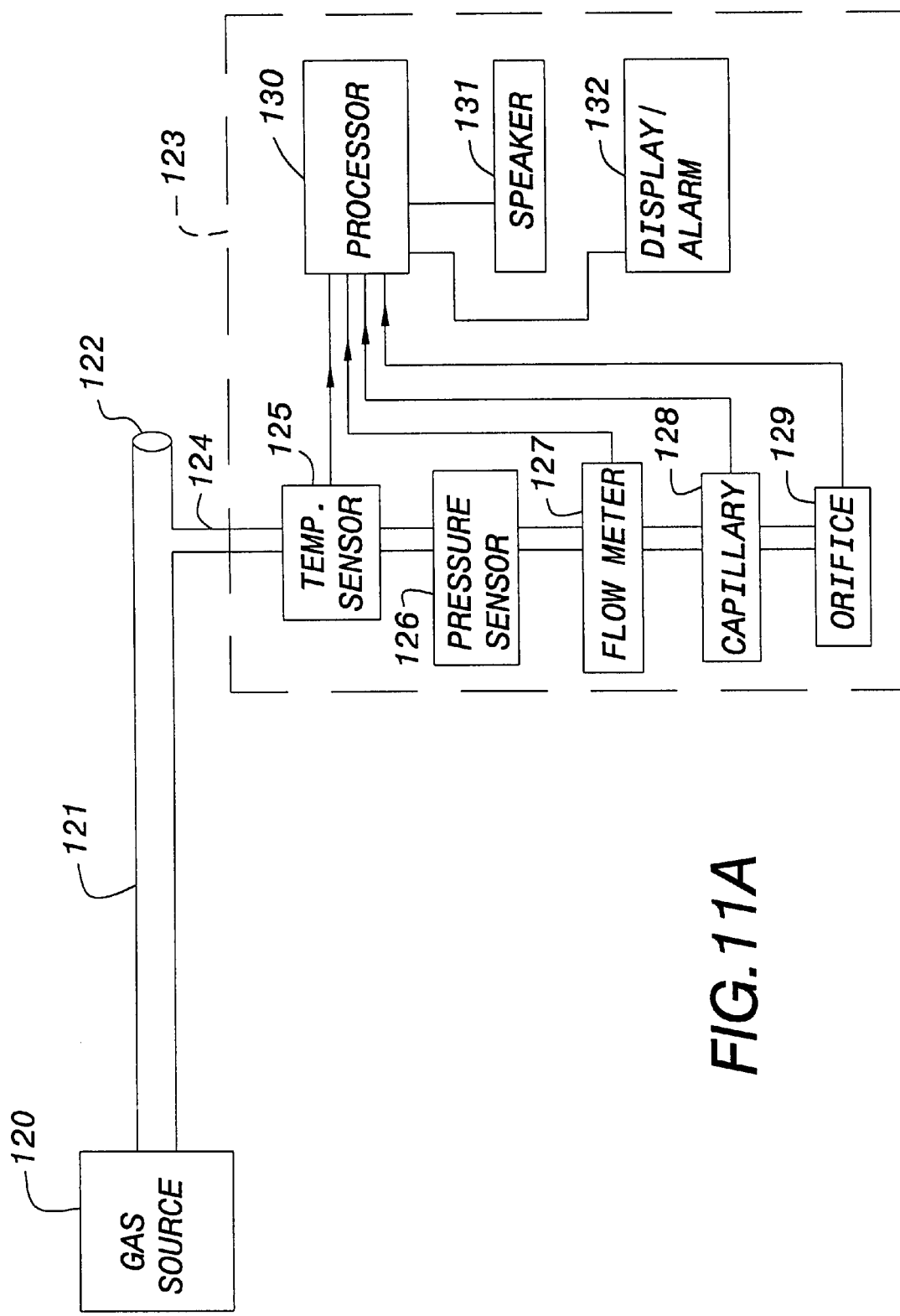
FIG. 11a is a diagrammatic representation of a gas identification device in accordance with an exemplary embodiment of the present invention.

FIG. 11a is a diagrammatic view illustrating a gas identification system according to the present invention. As shown in FIG. 11a, the gas identification system includes a gas source 120. The gas source 120 may be any type of container, or generator from which a single, pure gas (i.e., a gas consisting of a single constituent) is provided. For example, the source can be a pressurized tank of oxygen or nitrous oxide, or an oxygen generator. The gas from gas source 120 flows through gas supply line 121 (optional) to a gas outlet 122. The gas outlet 122 can be a wall outlet for providing oxygen or nitrous oxide or a coupler that connects a source of gas to an anesthesia delivery system. A portion of the gas flowing through gas supply line 121 is supplied to gas identifier 123 through a side stream sampling port 124.

The gas identifier 123 includes essentially the same sensors used in the three gas analyzer shown in FIG. 5*a* or FIG. 5*c*. Specifically, a temperature sensor 125 measures the temperature of the sample gas, a pressure sensor 126 measures the ambient pressure of the sample gas, a flow meter 127 measures the flow rate of the sample gas, and the pressure changes of the sample gas in a capillary 128 and across an orifice 129 are measured (of course, the oscillator can be used as the flowmeter and orifice as shown in FIG. 5*c*). The temperature sensor 125, pressure sensor, 126, flow meter 127, capillary 128 and orifice 129 each provide their respective measurements to processor 130 which determines the density and viscosity of the gas in accordance with equations 1–3 (or other equations relating density, viscosity and flow rate to temperature, oscillator frequency, and pressure drops across a capillary and an orifice).

The processor 130 includes a memory (e.g., a read-only memory) in which is stored the density and viscosity of the pure gas which is expected to be supplied (hereinafter, the expected gas) at outlet 122. The processor 130 compares the density and viscosity of the sample gas calculated from the measured temperature, flow rate and pressures with the stored density and viscosity values of the expected gas adjusted by the measured ambient conditions. If the calculated density value and the stored density value are essentially the same (i.e., their difference is less than a predetermined threshold value) and if the calculated viscosity value and stored viscosity value are essentially the same, the processor determines that the expected gas is being supplied at outlet 122. The gas identifier 123 can include a speaker 131 which produces an audible indication that the identity of the expected gas has been verified and/or a display 132 which produces a visible indication that the identity of the expected gas has been verified.

If either the density or viscosity calculated for the sample gas differs from the corresponding stored value of the expected gas, the processor 130 determines that the gas being supplied at outlet 122 is not a pure form of the expected gas. That is, a deviation of the density or viscosity of the sample gas from the known density or viscosity of the expected gas signifies that either the gas being supplied is not the expected gas or the gas being supplied contains other gasses in addition to the expected gas in a quantity sufficient to change the overall density and viscosity. For example, if nitrous oxide is erroneously supplied to an oxygen outlet, the processor 130 determines from the calculated density and viscosity that the sample gas is not the expected gas (oxygen). Likewise, if atmospheric air leaks into an otherwise pure oxygen supply through a rupture or faulty connection, the processor 130 determines that sample gas is not the expected gas (oxygen). When the processor 130 determines that the sample gas is not a pure form of the expected gas, the speaker 131 produces an audible alarm signal indicating that the gas being supplied differs from the expected gas, and the display 132 produces a corresponding visible indication. Optionally, the gas identifier 123 includes a mechanism for preventing the flow of the gas when such an error condition occurs, e.g., an automatic solenoid shut off value.

While it is possible to distinguish certain gasses based on only one fluidically determined property (i.e., density or viscosity), the fluidic measurement of two properties is preferable in order to ensure sufficient discrimination between different gasses. For example, several gasses, including some hydrocarbons, having molecular weights that are similar to that of oxygen (32). However, the viscosities of these gasses are significantly different from that of oxygen; thus, by measuring the density and viscosity of the sample gas, the identity of a gas such as oxygen can more readily be verified with accuracy.

Figure 11B:
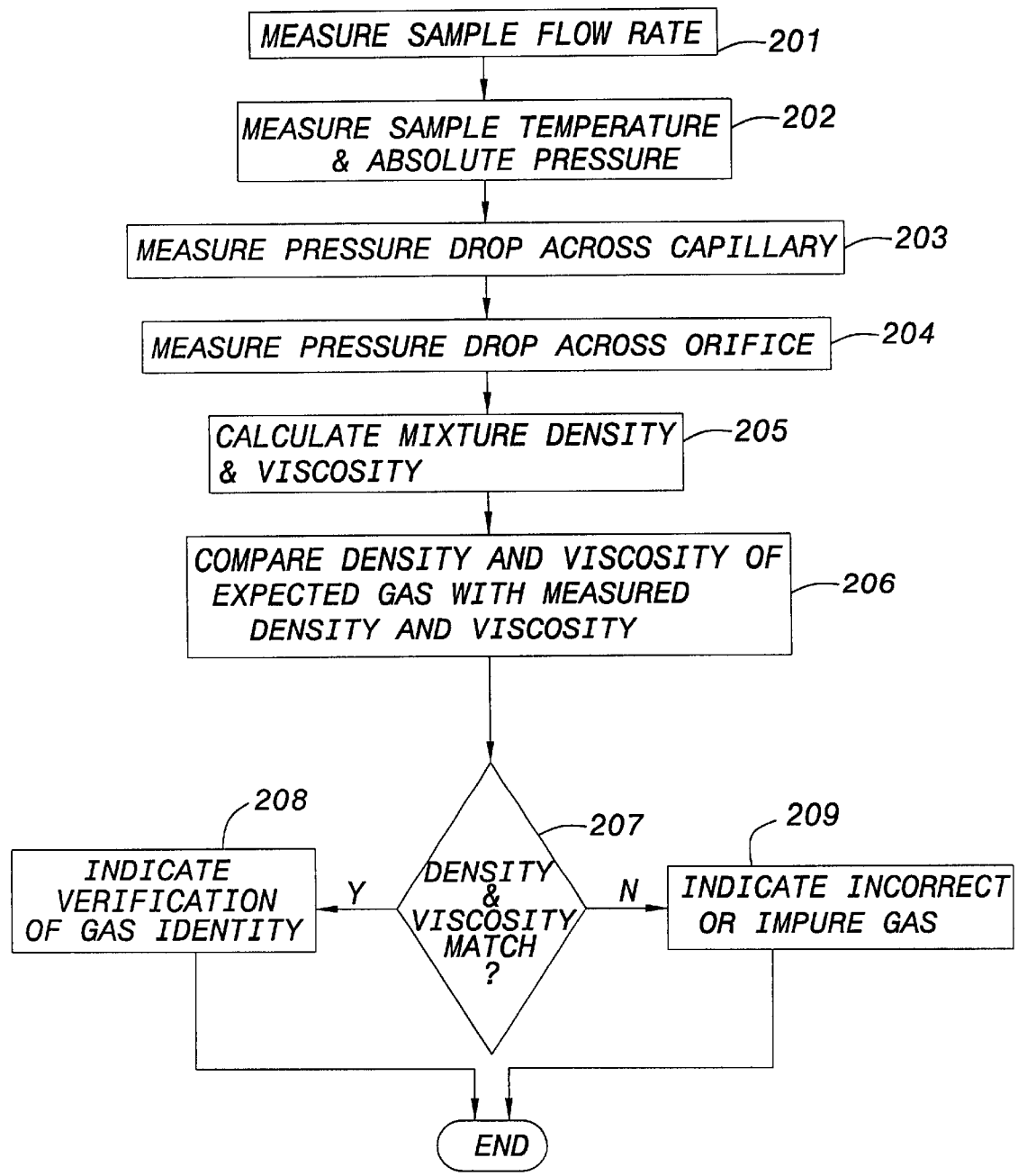
FIG. 11b is a flow chart summarizing the processing steps involved in determining or verifying the identity of a single, pure gas supplied from a source.

FIG. 11*b* is a flow chart summarizing the above-described processing steps (steps 201–209) involved in determining or verifying the identity of a single, pure gas supplied from a source.

In the above example, it is assumed that a particular gas is expected at the outlet 122, and the fluidically measured properties are compared to those of the expected gas to determine whether or not the actual gas is the expected gas. More generally, the gas identifier of the present invention can be programmed, such that the identity of any one of a number of gasses can be verified. Specifically, the memory of processor 130 can include a look-up table containing the densities and viscosities of all of the gasses that could be supplied to a point of delivery. An input device, such as a keyboard, touchpad or the like, can be used by an operator to select one of the gasses in the look-up table as the expected gas. The above-described density and viscosity comparisons are then performed using the stored density and viscosity values for the selected gas. Thus, the same gas identifier can be used to verify the identity of any one of several pure gasses.

Further, the gas identifier of the present invention can be used to determine the identity of an unknown pure gas. Specifically, the calculated density and viscosity of the measured sample gas is compared to the density and viscosity of each of the gasses stored in the look-up table. If the density and viscosity of the sample gas match those of one of the gasses in the look-up table, the gas identifier indicates the identity of the gas on the display 132.

In the above example, the density and viscosity of the single gas being analyzed are used to uniquely identify the gas, since these two properties clearly distinguish most gasses from one another and can be determined using measurement from inexpensive fluid sensors. It will be understood, however, that other combinations of gas properties can be used to identify a single gas. In particular, where certain gasses are more easily distinguishable from particular properties, those properties of the gas can be determined to identify the gas more readily. Table 2 provides a summary of properties (i.e., molecular weight, viscosity and specific heat) of selected respired gasses which can be used to distinguish various gasses.

TABLE 2

| GAS | MOLECULAR WEIGHT | VISCOSITY (20° C.) (kg/ms × 10$^{-5}$) | SPECIFIC HEAT (J/(kg ° K.)) |
|---|---|---|---|
| OXYGEN | 32.000 | 2.0238 | 906.853 |
| NITROGEN | 28.016 | 1.7390 | 1031.35 |
| NITROGEN w/ air traces | 28.155 | 1.7702 | 1055.24 |
| CARBON DIOXIDE | 44.010 | 1.4660 | 844.348 |
| NITROUS OXIDE | 44.016 | 1.4607 | 850.716 |
| CARBON MONOXIDE | 28.010 | 1.6609 | 1057.11 |

TABLE 2-continued

| GAS | MOLECULAR WEIGHT | VISCOSITY (20° C.) (kg/ms × 10$^{-5}$) | SPECIFIC HEAT (J/(kg ° K.)) |
|---|---|---|---|
| WATERVAPOR | 18.016 | 1.0522 | 1881.43 |
| HALOTHANE | 197.40 | 1.1191 | 524.479 |
| DESFLURANE | 168.04 | TBD | TBD |
| ISOFLURANE | 184.49 | 1.0273 | 750.797 |
| SEVOFLURANE | 200.05 | TBD | TBD |

For example, in the case of $CO_2$ and $N_2O$, the properties of viscosity and specific heat at a constant pressure or at a constant volume (calculated from the sonic oscillator frequency measurement) more clearly distinguish these gasses from each other than the properties of density and viscosity. Thus, measurements from a sonic oscillator could be used instead of measurements from a densitometer orifice. Of course, using a sensor package such as that shown in FIG. 9a or 9c, any set of measured properties which sufficiently distinguishes the possible gasses being supplied can be used to identify the gas. Thus, it should be understood that the sensor package can be used in a variety of contexts without any hardware modifications; only the software used to analyze the measured results is modified for different applications.

In the medical field, the gas identifier of the present invention can be used to identify any of a number of pure gasses. For example, gasses such as oxygen, nitrous oxide, and volatile anesthesia gasses are supplied from sources to patients in operating rooms, intensive care units and hospital rooms. The gas identifier can be positioned at any point in the system where the gas to be identified should be present in a pure form. For example, where oxygen is supplied from a remote source to a wall outlet, the gas identifier may be directly integrated into the wall outlet.

Alternatively, the gas identifier can be a separate unit which can be connected to an existing wall outlet. According to this alternative, the gas identifier includes an upstream terminal which couples to the wall outlet and a downstream terminal which is similar to the wall outlet, so that the gas identifier can be connected in series between the wall outlet and a local supply line which mates with the downstream terminal of the gas identifier.

Since only a small fraction of the gas being supplied is required to determine or verify the identity of the gas, it is preferable in some circumstances that the gas identifier operate continuously while the gas is actually being supplied rather than "off-line" or prior to actual delivery of the gas. For example, in the case of a wall outlet oxygen supply, continuous operation of the gas identifier during gas delivery is desirable, since a leak of atmospheric air into the oxygen supply can be detected at anytime during oxygen delivery. Optionally, the pressure in the main gas flow stream can be used to run a turbine or other electrical generator that generates the electricity necessary to operate the sensors and processor of the gas identifier. Alternatively, the electricity can be provided by a battery, an AC power source or other conventional power source.

The gas identifier of the present invention advantageously prevents errors in administering gasses in medical settings. Because the present invention uses fluidic sensors (which are inexpensive), the gas identifier of the present invention can be implemented at a fraction of the cost of a gas identifier that uses conventional techniques, such as spectroscopy. Thus, the gas identifier of the present invention can affordably be incorporated in oxygen supply outlets and anesthesia delivery devices throughout a hospital. Further, unlike gas analyzers that use one or more of the aforementioned conventional techniques, the gas identifier of the present invention does not require periodic servicing for calibration, and therefore requires less maintenance.

Extending the principles used to identify a single constituent gas, in accordance with the present invention, the above-described sensors can be used to identify an unknown gas mixed with other, known gasses. By way of illustrative example, consider a two-gas mixture, such as the gas mixture produced by a vaporizer, consisting of an anesthetic agent and oxygen which is used as a carrier gas to drive the vaporizer. The following process can be used to verify or determine the identity of the anesthetic agent to prevent inadvertent administration of the wrong agent. Using, for example, the flow meter-capillary-orifice arrangement shown in FIG. 5a or FIG. 5c (i.e., a three-gas analyzer), the density and viscosity of the gas mixture as a whole are determined (see equations 1–3). One of the two constituents is known to be oxygen. The other constituent is then assumed to be a particular default anesthetic agent ($A_1$) (in general one of four: halothane, isoflurane, desflurane and sevoflurane). Using this assumption, the concentrations of oxygen and agent $A_1$ are determined by solving only the density equation (using equation 4 with the assumption that the density of the unknown gas is that of agent $A_1$) and the constitutive equation (equation 6) for the two unknown concentrations. Next, the viscosity equation (equation 5) together with the computed concentrations are used to compute the absolute viscosity of the unknown anesthetic agent. The computed viscosity of the unknown agent is compared to the known (stored in memory) viscosity of the anesthetic agent $A_1$. If the computed and known viscosities match (i.e., their difference falls within a predetermined threshold value), it is determined that the anesthetic agent is, in fact, agent $A_1$. If the computed viscosity and the known viscosity for agent $A_1$ do not match, it is determined that the unknown agent is not agent $A_1$, and the process is repeated with other agents $A_2, A_3, \ldots, A_L$ until a match is found.

Figure 12:
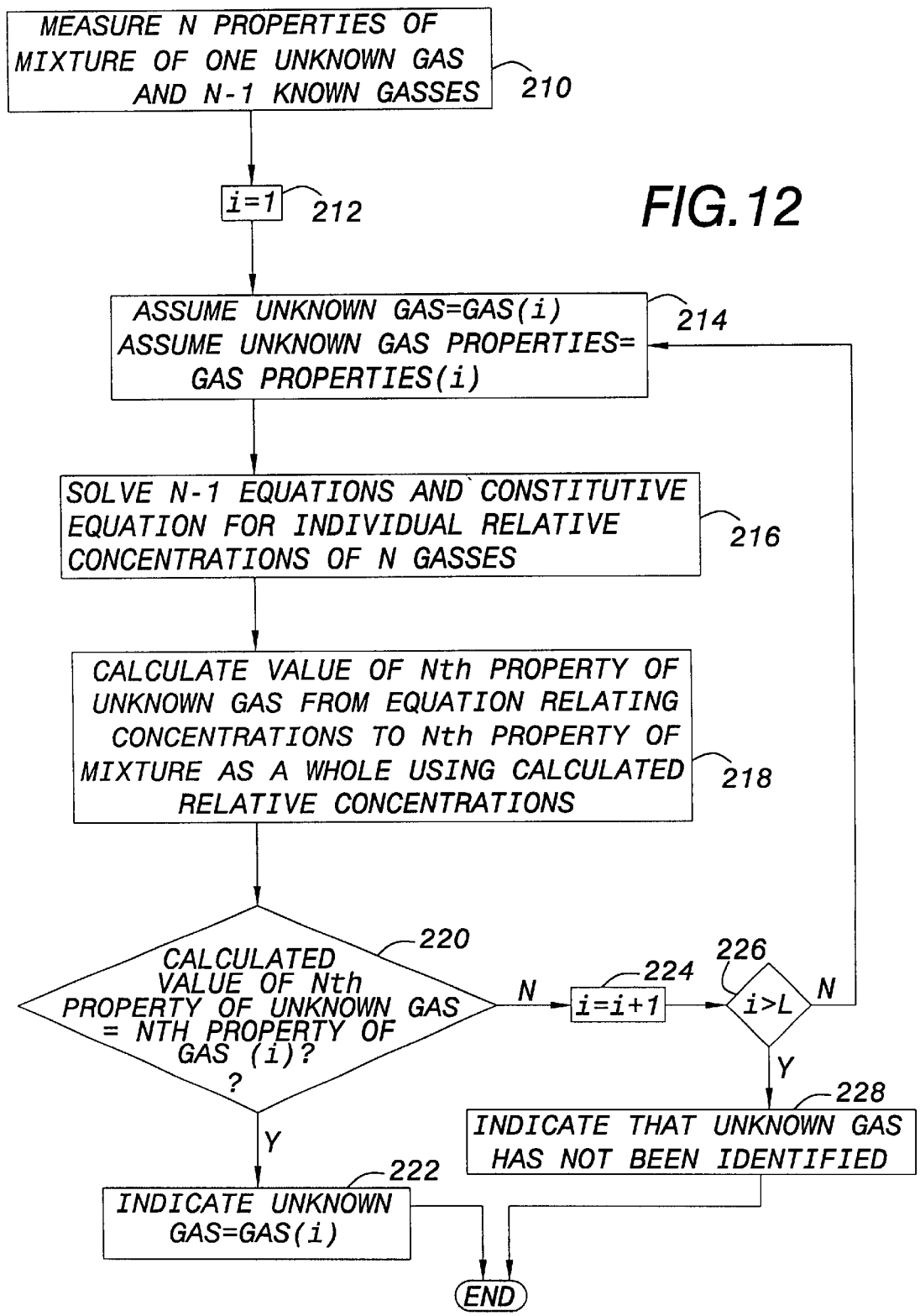
FIG. 12 is a function flow diagram illustrating the processing steps required to determine the absolute identity of an unknown gas in a mixture of gasses in accordance with one embodiment of the present invention.

In general, in a mixture of N gasses in unknown concentrations, where the identities of N-1 gasses are known and the identity of one gas is unknown, the identity of the one unknown gas can be determined with an N+1 gas analyzer in accordance with the process summarized in the flow chart illustrated in FIG. 12. In a first step 210, N properties of the mixture are determined. For example, the density, viscosity and specific heat of the mixture (N=3) as a whole can be determined using the above-described oscillator-capillary-sonic oscillator sensors. Further, concentrations of individual gasses can be determined using other, conventional sensors or other independently measured properties of the mixture as whole, which properties relate to relative concentrations. For example, the mixture could consist of three (N=3) gasses: oxygen, carbon dioxide and an anesthesia agent, where the anesthesia agent is assumed to be initially unknown. The three properties measured by a four-gas analyzer could be, for example: density, viscosity, and specific heat.

The unknown gas is then assumed to be one of a set of possible gasses. Specifically, a list of L gasses and their known properties are stored in a memory. For example, where the unknown gas is an anesthetic agent, a list of five or six anesthesia agents (e.g., halothane, enflurane, isoflurane, methoxyflurane, desflurane, sevoflurane) and their properties (e.g., density, viscosity and ratio of specific heats) are stored in a look-up table in a memory. In step 212, a counter i, which indexes the look-up table, is initialized to a value of one, corresponding to a first anesthetic agent $A_1$ in the look-up table (i.e., the default agent, which can be, for example, anesthesia agent marked on the label of the container).

In step 214, the value of counter i (initially equal to one) is used to retrieve the name and properties of gas i in the look-up table, and the identity of the unknown gas is assigned (i.e., temporarily assumed to be) that of gas i, with the properties of the unknown gas being assigned the values of the properties of gas i retrieved from the look-up table. Initially, the value of i is set to one; thus, the unknown gas is assumed to be the default gas $A_1$ in the look-up table, and the properties of the unknown gas are assumed to be those of the default gas $A_1$.

In step 216, N-1 of the N properties are used to form N-1 equations relating to the relative concentrations, which, together with the constitutive equation (equation 6) are solved for the N relative concentrations of the N gasses in the mixture, using the assumption that the unknown gas has the properties of the gas $A_i$. For example, the equations for density, specific heat, and the constitutive equation can be used to calculate the relative concentrations of the oxygen, carbon dioxide and gas $A_i$. Note that the viscosity information (in this example) is not used in this step.

At this point, the only unknown in the equation which relates the Nth property of the mixture as a whole to the individual constituent concentrations is the Nth property of the unknown gas. Thus, in step 218, this equation can be solved for the Nth property of the unknown gas by inserting the calculated concentrations and the measured Nth property of the mixture as a whole (note that this equation was not used to determine the relative concentrations). For example, using equation (5), the viscosity of the unknown gas (assumed to be agent $A_i$ for purposes of computing concentrations) can be calculated from the viscosity equation (equation (5)) of the mixture and the computed concentrations of oxygen, carbon dioxide and gas $A_i$.

In step 220, the calculated Nth property of the unknown gas is compared to the known (stored) Nth property of gas $A_i$. If the value of the calculated property N of the unknown gas matches the value of (known) property N of gas $A_i$, it is determined that the unknown gas is gas $A_i$. In this case, it is indicated (on a display or the like) in step 222 that the unknown gas is gas $A_i$, and the identification process ends.

If the value of the calculated property N of the unknown gas does not match the value of (known) property N of gas $A_i$, it is determined that the unknown gas is not gas $A_i$. In this case, in step 224, the index counter i is incremented, and, in step 226, the index counter i is compared to the number L of gasses in the look-up table. If the index counter i is not greater than L, processing returns to step 214, and the process is repeated with the incremented value of i. If, on the other hand, the index counter i is determined to be greater than L in step 226, it is indicated in step 228 (on a display and/or by aural alarm) that the unknown gas has not been identified, and the identification process ends. Optionally, even where the identity of the gas is determined, an alarm (visual and/or aural) can be set off when the unknown gas is determined to be other than the default gas to indicate that the identity of the gas is other than the expected (default) gas.

Importantly, the above method of identifying an unknown constituent in a mixture can be carried out with the same hardware used to determine the concentrations of N known gasses (e.g., the sensor suites shown in FIGS. 5a/5c and 9a/9c). Only the processing software run on the signal processor is different. That is, to determine concentrations of known constituents, N-1 properties of the gas mixture are measured and N equations (including the constitutive equation) are solved for N unknown concentrations of N known constituents. In contrast, to identify an unknown constituent: N properties of the gas mixture are measured; N-1 of the properties are used to generate N-1 equations which, together with the constitutive equation, are solved for N concentrations, where the properties of the unknown constituent are assumed to be those of a particular gas; the N concentrations and the Nth property of the mixture are used to calculate the Nth property of the unknown gas which is then compared to the known Nth property of the gas assumed to be the unknown gas (for purposes of calculating the concentrations); and different gasses are tried (assumed to be the unknown gas) in this process until the comparison yields a match or all potential gasses have been tried without a successful match.

Note that the process of identifying an unknown, pure (single constituent) gas (FIG. 11b) is essentially a special case of the process shown in FIG. 12, where N=1, although more than one property is preferably measured to provide greater discrimination between different gasses (also, it is unnecessary in this case to solve for the concentrations, since the concentration of the single constituent is unity).

The same hardware may also be used to identify a mixture of two unknown gasses. In this case, the process is essentially the same as that described above; however, the trial and error technique of trying each potential gas as the unknown gas until a match is found is expanded, such that the calculations are performed by substituting a pair of gasses for the two unknown gasses until a match is found or every potential combination of two gasses has been tried. For example, where the two unknown gasses are two of five (six) possible gasses, at most 10(15) iterations are necessary to try every combination. Given that the two unknown gasses are two members of a set of gasses whose properties are known (and distinguishable), the identities and concentrations of the two unknown gasses in a mixture can be determined by measuring three properties of the mixture, since four equations (including the constitutive equation) can be uniquely solved for four unknowns (two unknown concentrations and two unknown identities). In general, in a mixture of fluids where concentrations of L fluids are unknown and identities of M fluids are unknown, the unknown concentrations and identities can be determined by measuring N-1 bulk properties of the mixture and by solving N equations (inclusive of the constitutive equation), where N=L+M (as used here, N does not necessarily represent the number of fluids in the mixture).

According to another embodiment of the present invention, the same hardware can be used to identify an unknown gas in a mixture of N gasses (including N-1 known gasses) using an N-gas analyzer measuring N-1 gas properties (i.e., by measuring one less property than in the gas identification method described above). This technique is particularly useful where the unknown gas is known to have a value of at least one property that is significantly different from the value of that property of the other gasses in the mixture. For example, the technique is suitable for identifying an anesthetic agent in a mixture of respired gasses, where the anesthetic agent has a significantly higher density than the other gasses.

Figure 13:
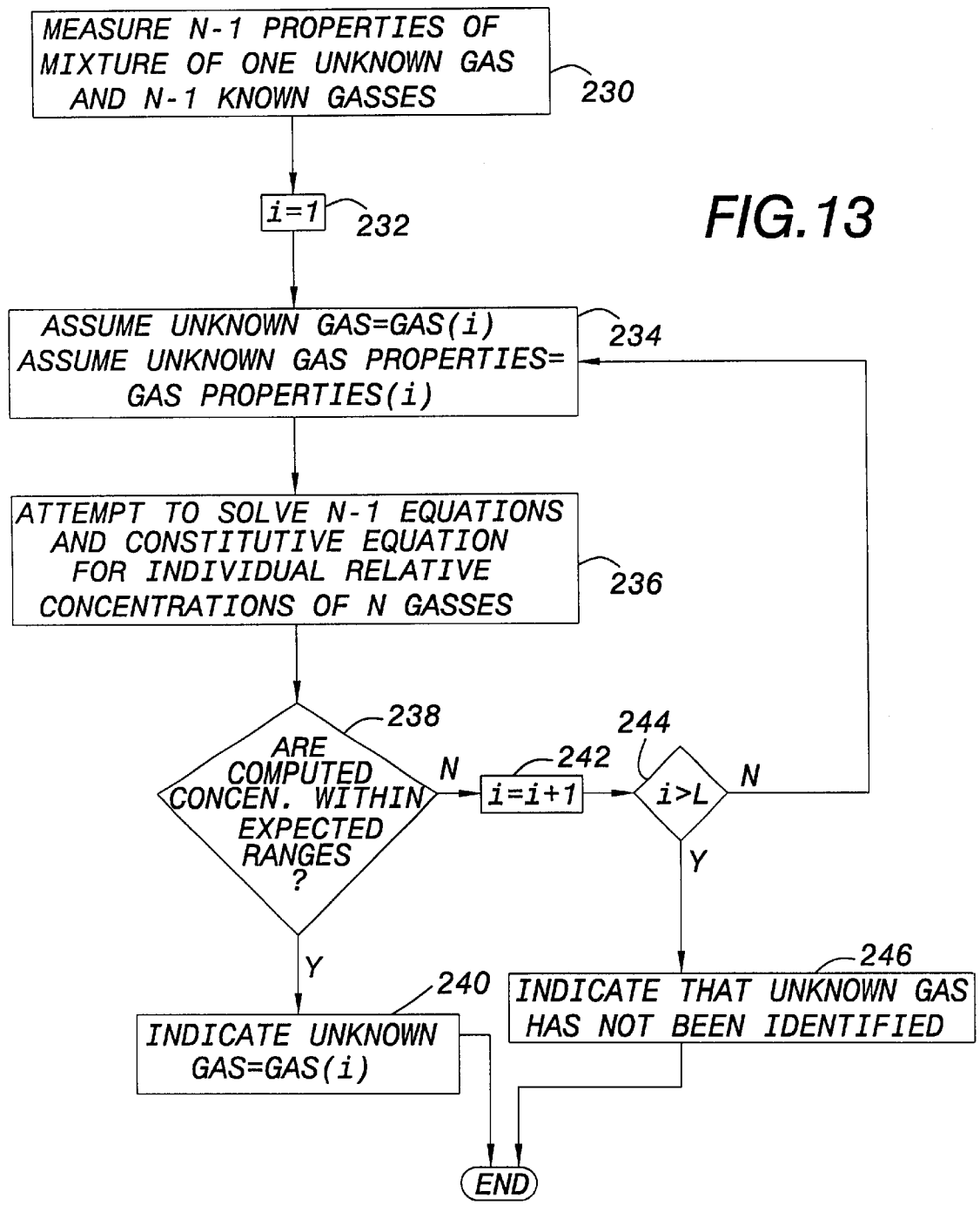
FIG. 13 is a function flow diagram illustrating the processing steps required to determine the probable identity of an unknown gas in a mixture of gasses in accordance with another embodiment of the present invention.

More specifically, as shown in FIG. 13, according to this embodiment, in a first step 230, N-1 properties of the mixture are determined using an N-gas analyzer. For example, the density, viscosity and specific heat of the mixture as a whole can be determined using the above-described oscillator-capillary-sonic oscillator sensors. Further, concentrations of individual gasses can be determined using other, conventional sensors or other properties of the mixture as whole, which properties relate to relative concentrations. Also, in the case of anesthesia administration, the above described technique for discriminating carbon dioxide and nitrous oxide can be employed. For example, the mixture could consist of five (N=4) gasses: nitrogen, oxygen, carbon dioxide/nitrous oxide, and an anesthesia agent, where the anesthesia agent is assumed to be initially unknown. The three properties measured by the gas analyzer could be, for example: density, viscosity and the specific heat.

The unknown gas is then assumed to be one of a set of possible gasses. Specifically, a list of L gasses and their known properties are stored in a memory. For example, where the unknown gas is an anesthetic agent, a list of five or six anesthesia agents (e.g., halothane, enflurane, isoflurane, methoxyflurane, desflurane, sevoflurane) and their properties (e.g., density, viscosity, specific heat) are stored in a look-up table in a memory. In step 232, a counter i, which indexes the look-up table, is initialized to a value of 1, corresponding to a first anesthetic agent $A_1$ in the look-up table (i.e., the default agent).

In step 234, the value of counter i (initially equal to one) is used to retrieve the name and properties of gas i in the look-up table, and the identity of the unknown gas is assigned (i.e., temporarily assumed to be) that of gas i, with the properties of the unknown gas being assigned the values of the properties of gas i retrieved from the look-up table. Initially, the value of i is set to one; thus, the unknown gas is assumed to be the default gas $A_1$ in the look-up table, and the properties of the unknown gas are assumed to be those of the default gas $A_1$.

In step 236, using the assumption that the unknown gas has the properties of the gas $A_i$, the N-1 properties are used to form N-1 equations relating to the relative concentrations, which, together with the constitutive equation (equation 6) form N equations, and an attempt is made to solve the N equations for the relative concentrations of the constituents of the mixture. For example, the equations for density, viscosity, specific heat and the constitutive equation can be used to calculate the relative concentrations of nitrogen, oxygen, carbon dioxide/nitrous oxide and gas $A_i$.

It has been found by the present inventor that, provided that a sufficient concentration (e.g., at least approximately 2–5%) of the unknown gas is present, the equations yield individual gas concentrations that fall within expected or reasonable ranges only when the properties of the unknown gas are assumed to be those of the correct gas in the equations. If the properties of the wrong gas are used, the equations yield at least one gas concentration that is not within its expected range or, mathematically, is not between zero and one. Thus, if the solution of the equations yield concentrations within expected ranges, it is assumed that the unknown gas is indeed the gas $A_i$. In practice, expected ranges of concentrations of individual gasses can be stored or pre-programmed into the system for comparison with the computed concentrations in order to determine whether the computed concentrations are reasonable. Other out of bounds conditions may be very high $CO_2$ or agent concentrations.

In step 238, if the solution to the equations yields concentrations that are within expected ranges, it is determined that the unknown gas is gas $A_i$. In this case, in step 240, it is indicated (on a display or the like) that the unknown gas is gas $A_i$, and the identification process ends.

If the solution to the equations fails to converge to meaningful concentration values (i.e., at least one constituent concentration is outside its expected range), it is determined that the unknown gas is not gas $A_i$. In this case, in step 242, the index counter i is incremented, and in step 244, the index counter i is compared to the number L of gasses in the look-up table. If the index counter i is not greater than L, processing returns to step 234, and the process is repeated with the incremented value of i. If, on the other hand, the index counter i is determined to be greater than L in step 244, it is indicated in step 246 (on a display and/or by aural alarm) that the unknown gas has not been identified, and the identification process ends.

The approach of the present invention provides a simple apparatus and method to measure concentrations of several medical gasses and to identify individual gasses at a relatively low cost. Although the above description is primarily concerned with medical gas analyzers, the present invention is not limited to the preferred embodiment but is applicable to other gas analysis applications, including, but not limited to, industrial production of gasses, atmospheric analysis, pollution tracking and other applications for the detection and analysis of chemical and biological agents. In addition, the present invention is not limited to a specific number of gasses that are in a mixture or for that matter only fluidic sensors, but rather, since bulk properties of gasses can be measured using a variety of low cost electronic and hybrid electro-fluidic devices, the present invention may extend to low cost scientific gas analysis of large numbers of gasses.

Furthermore, the present invention is not limited to the analysis of only gasses because it should be recognized that substantially the same methods and apparatus may be applied to the analysis of mixtures of liquid fluids as well, as long as sufficient differences in mixture bulk properties will occur due to the changes of concentrations of the constituents of the fluids. More specifically, the density and viscosity of a liquid can be measured and determined in accordance with equations (1)–(3) with measurements from the fluidic sensors (flow meter, capillary and orifice) described herein. Other suitable sensors can be used to measure other properties of a mixture of liquids which relate to constituent concentrations or which can be used to uniquely identify an unknown liquid constituent in accordance with the above described techniques.

Having described preferred embodiments of a new and improved method and apparatus for real time gas analysis using fluidic sensors, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. Method of determining whether a fluid flowing from a source is an expected, single-constituent fluid, the method comprising the steps of:

a) measuring the flow rate of the fluid;

b) measuring a pressure drop of the fluid across an orifice;

c) measuring a pressure drop of the fluid across a capillary;

d) computing at least one property of the fluid from the flow rate, the orifice pressure drop and the capillary pressure drop, said at least one property including at least one of density and viscosity; and e) if each of said at least one property of the fluid is within a predetermined threshold of a value of a corresponding property of the expected, single-constituent fluid, indicating that the fluid is the expected, single-constituent fluid.

2. The method of claim 1, further comprising:
f) indicating that the fluid is not the expected, single-constituent fluid if any of said at least one property of the fluid is not within a predetermined threshold of a value of a corresponding property of the expected, single-constituent fluid.

3. The method of claim 1, further comprising:
f) inhibiting a flow of the fluid if any of said at least one property of the fluid is not within a predetermined threshold of a value of a corresponding property of the expected, single-constituent fluid.

4. The method of claim 1, further comprising:
f) actuating an aural or visual alarm if any of said at least one property of the fluid is not within a predetermined threshold of a value of a corresponding property of the expected, single-constituent fluid.

5. The method of claim 1, wherein the method is performed repeatedly while the fluid is flowing.

6. The method of claim , wherein step a) includes measuring the flow rate of the fluid through a fluidic flowmeter.

7. The method of claim 1, further comprising:
f) measuring an acoustic frequency of the mixture; and
wherein step d) includes computing from the acoustic frequency the specific heat of the fluid as one of said at least one property of the fluid.

8. The method of claim 1, wherein, if any of said at least one property of the fluid is not within a predetermined threshold of a value of a corresponding property of the expected, single-constituent fluid, the method further comprises:
f) comparing each of said at least one property of the fluid to a value of a corresponding property of a second, single-constituent fluid; and
g) if each of said at least one property of the fluid is within a predetermined threshold of a value of a corresponding property of the second, single-constituent fluid, indicating that the fluid is the second, single-constituent fluid.

9. The method of claim 1, wherein said expected, single-constituent fluid is oxygen.

10. The method of claim 1, wherein said expected, single-constituent fluid is nitrous oxide.

11. The method of claim 1, wherein said expected, single-constituent fluid is a volatile anesthesia gas.

12. An apparatus for determining whether a fluid flowing from a source is an expected, single-constituent fluid, comprising:
a flowmeter configured to measure the flow rate of the fluid;
an orifice and a first sensor configured to measure a pressure drop of the fluid across the orifice;
a capillary and a second sensor configured to measure a pressure drop of the fluid across a capillary; and
a processor configured to: compute at least one property of the fluid from the flow rate, the orifice pressure drop and the capillary pressure drop, said at least one property including at least one of density and viscosity; and determine that the fluid is the expected, single-constituent fluid if each of said at least one property of the fluid is within a predetermined threshold of a value of a corresponding property of the expected, single-constituent fluid.

13. The apparatus of claim 12, wherein the apparatus is configured to receive the fluid flowing from a pressurized tank.

14. The apparatus of claim 12, wherein the apparatus is configured to receive the fluid flowing from a supply line.

15. The apparatus of claim 12, wherein the apparatus is configured to receive the fluid flowing from a wall outlet supplying the fluid.

16. The apparatus of claim 12, wherein the apparatus further comprises:
an upstream terminal connectable to the source; and
a downstream terminal connectable to a local supply line.

17. The apparatus of claim 12, wherein the apparatus operates continuously while fluid is flowing from the source.

18. The apparatus of claim 12, wherein the apparatus repeatedly determines whether the fluid flowing from the source is the expected, single-constituent fluid.

19. The apparatus of claim 12, wherein the apparatus operates using electricity generated from pressure from flow of the fluid.

20. The apparatus of claim 12, wherein said processor determines that the fluid is not the expected, single-constituent fluid if any of said at least one property of the fluid is not within a predetermined threshold of a value of a corresponding property of the expected, single-constituent fluid.

21. The apparatus of claim 12, wherein said processor commands that the flow of the fluid be inhibited if any of said at least one property of the fluid is not within a predetermined threshold of a value of a corresponding property of the expected, single-constituent fluid.

22. The apparatus of claim 12, further comprising an alarm that is actuated if any of said at least one property of the fluid is not within a predetermined threshold of a value of a corresponding property of the expected, single-constituent fluid.

23. The apparatus of claim 22, wherein said alarm includes a visual display.

24. The apparatus of claim 22, wherein said alarm includes an audible sound.

25. The apparatus of claim 12, wherein said expected, single-constituent fluid is oxygen.

26. The apparatus of claim 12, wherein said expected, single-constituent fluid is nitrous oxide.

27. The apparatus of claim 12, wherein said expected, single-constituent fluid is a volatile anesthesia gas.

28. The apparatus of claim 12, wherein said flowmeter includes a fluidic oscillator through which the fluid flows and a plurality of microphones adapted to measure an oscillation frequency of the fluid in the fluidic oscillator.

29. The apparatus of claim 28, wherein a nozzle of said fluidic oscillator serves as said orifice.

30. The apparatus of claim 28, wherein said fluidic oscillator is a fluidic amplifier feedback oscillator flowmeter.

31. The apparatus of claim 12, wherein said capillary is one of a plurality of capillaries arranged to provide parallel resistance to flow of the mixture through said capillaries.

32. The apparatus of claim 12, further comprising a sonic oscillator and a third sensor configured to measure an acoustic frequency of the fluid flowing through said sonic oscillator, wherein said processor computes from the acoustic frequency the specific heat of the fluid as one of said at least one property of the fluid.

33. The apparatus of claim 12, wherein, if any of said at least one property of the fluid is not within a predetermined threshold of a value of a corresponding property of the expected, single-constituent fluid, said processor: compares each of said at least one property of the fluid to a value of a corresponding property of a second, single-constituent fluid, and determines that the fluid is the second, single-constituent fluid if each of said at least one property of the fluid is within a predetermined threshold of a value of a corresponding property of the second, single-constituent fluid.

* * * * *